(12) United States Patent
Hoshi

(10) Patent No.: US 9,751,912 B2
(45) Date of Patent: Sep. 5, 2017

(54) NEUROTOXIC TARGET FOR AMYLOSPHEROID, METHOD AND MATERIAL FOR REDUCING THE NEUROTOXICITY OF AMYLOSPHEROID, AND USE THEREOF

(71) Applicant: TAO Health Life Pharma Co., Ltd.

(72) Inventor: Minako Hoshi, Kyoto (JP)

(73) Assignee: TAO HEALTH LIFE PHARMA CO., LTD., Kyoto (JP)

( * ) Notice: Subject to any disclaimer, the term of this patent is extended or adjusted under 35 U.S.C. 154(b) by 0 days.

(21) Appl. No.: 13/729,152

(22) Filed: Dec. 28, 2012

(65) Prior Publication Data

US 2013/0171069 A1 Jul. 4, 2013

Related U.S. Application Data

(60) Provisional application No. 61/581,267, filed on Dec. 29, 2011.

(30) Foreign Application Priority Data

Jan. 10, 2012 (JP) ................................ 2012-002448

(51) Int. Cl.

| | |
|---|---|
| *A61K 51/08* | (2006.01) |
| *A61K 38/13* | (2006.01) |
| *A61K 38/00* | (2006.01) |
| *C07K 5/117* | (2006.01) |
| *A61K 38/17* | (2006.01) |
| *A61K 31/554* | (2006.01) |
| *G01N 33/68* | (2006.01) |
| *C07K 7/06* | (2006.01) |
| *C07K 7/08* | (2006.01) |
| *C07K 5/107* | (2006.01) |
| *C07K 5/11* | (2006.01) |

(52) U.S. Cl.
CPC .......... *C07K 5/1024* (2013.01); *A61K 31/554* (2013.01); *A61K 38/13* (2013.01); *A61K 38/1767* (2013.01); *A61K 51/08* (2013.01); *C07K 5/1016* (2013.01); *C07K 5/1019* (2013.01); *C07K 7/06* (2013.01); *C07K 7/08* (2013.01); *G01N 33/6896* (2013.01); *A61K 38/00* (2013.01); *G01N 2500/02* (2013.01); *G01N 2800/2821* (2013.01)

(58) Field of Classification Search
None
See application file for complete search history.

(56) References Cited

U.S. PATENT DOCUMENTS

| | | |
|---|---|---|
| 5,866,363 A | 2/1999 | Pieczenik |
| 6,525,174 B1 | 2/2003 | Young et al. |
| 6,921,655 B1 | 7/2005 | Nakamura et al. |
| 8,168,188 B1 | 5/2012 | Hoshi et al. |
| 2003/0194414 A1* | 10/2003 | Bogoch .................. C07K 14/34 424/204.1 |
| 2010/0095387 A1 | 4/2010 | Smith et al. |
| 2010/0297662 A1 | 11/2010 | Hoshi et al. |

FOREIGN PATENT DOCUMENTS

| | | |
|---|---|---|
| JP | 2008-291025 | 12/2008 |
| WO | 2006/016644 | 2/2006 |
| WO | 2006/079076 | 7/2006 |
| WO | WO2006110496 | * 10/2006 |
| WO | 2009/018179 | 2/2009 |
| WO | 2009/057664 | 5/2009 |
| WO | WO2010083842 | * 7/2010 |

OTHER PUBLICATIONS

Alz.org 2012 "Dementia with lewy bodies (DLB) | Signs, symptoms, and diagnosis" accessed from http://www.alz.org/dementia/dementia-with-lewy-bodies-symptoms.asp on Jan. 16, 2014.*
Rafii and Aisen 2009 "Recent developments in Alzheimer's disease therapeutics" BMC medicine 7:7.*
Janeway et al. 2001 "Immunobiology: the immune system in health and disease" Garland Science, New York. 5th ed.*
Gassama-Diagne 1989 "Purification of a new calcium-independent high molecular weight phospholipase A2/lysophospholipase (phospholipase B) from guinea pig intestinal brush-border membrane" JBC 264(16):9470-9475.*
Lotan 1993 "Lectins and Glycobiology. Chapter 20:Analysis of lectin expression by immunoblotting" Gablius et al. copywrite Springer-Verlag Berlin Heidelberg.*
Holt 2003 "Domain antibodies: proteins for therapy" Trends in Biotech 21(11):484-490.*
A. Noguchi et al., "Isolation and Characterization of Patient-Derived, Toxic, High Mass Amyloid β-Protein (Aβ) Assembly from Alzheimer Disease Brains", Journal of Biological Chemistry, vol. 284, No. 47, pp. 32895-32905, Nov. 20, 2009.
G. M. Shankar et al., "Amyloid-β Protein Dimers Isolated Directly from Alzheimer's Brains Impair Synaptic Plasticity and Memory" Nature Medicine, vol. 14, No. 8, pp. 837-842, Aug. 2008.
M. Hoshi et al., "Spherical Aggregates of β-amyloid (Amylospheroid) Show High Neurotoxicity and Activate tau Protein Kinase I/Glycogen Synthase Kinase-3β", Proc. Nat'l. Acad. Sci., vol. 100, No. 11, pp. 6370-6375, May 27, 2003.

(Continued)

*Primary Examiner* — Adam M Weidner
(74) *Attorney, Agent, or Firm* — Wenderoth, Lind & Ponack, L.L.P.

(57) ABSTRACT

In one or a plurality of embodiments, there is provided a target molecule of amylospheroid, which is expressed in mature neurons and to which the amylospheroid binds to induce death of cells. Further, in one or a plurality of embodiments, there is provided a method and a substance for inhibiting death of mature neurons induced by the amylospheroid. In one aspect, the present disclosure relates to a use of $Na^+/K^+$-ATPase α3 as a binding target molecule of amylospheroid. In another aspect, the present disclosure relates to a method for suppressing death of mature neurons induced by the amylospheroid, including inhibiting protein-protein interaction between the amylospheroid and the $Na^+/K^+$-ATPase α3, and the like.

8 Claims, 12 Drawing Sheets

(56) References Cited

OTHER PUBLICATIONS

S. Matsumura et al., "Two distinct Amyloid (Aβ) Assembly Pathways Leading to Oligomers and Fibrils Identified by Combined Fluorescence Correlation Spectroscopy, Morphology and Toxicity Analyses", The Journal of Biological Chemistry, vol. 286, No. 13, pp. 11555-11562, Apr. 1, 2011.
International Search Report issued in International (PCT) Application No. PCT/JP2012/083271.
K. Hirota et al., "Pseudomonas Alcaliphila gyrB Gene for DNA Gyrase Subunit B, Partial cds", NCBI Entrez Nucleotide, Accession No. AB494446, Aug. 19, 2011.
M. Hoshi et al., "Determination of State of Alzheimer's Disease by Structural Biological Approach and Development of Molecularly-Targeted Therapy", Research of New Medical Devices, vol. 16, p. 28, Mar. 25, 2011 with partial English translation.
M. Hoshi et al., "Study on Determination of State of Alzheimer's Disease by Structural Biological Approach and Development of Molecularly-Targeted Therapy", Health and Labor Sciences Research Grant (Medical Equipment Development Promotion Research Project) Summary Research Report, May 2011, pp. 1-8 with partial English translation.
Extended European Search Report dated Jun. 2, 2015, issued in corresponding European Patent Application No. 12862008.5.
Reina et al., "Expression of the α3/β1 isoform of human Na,K-ATPase in the methylotrophic yeast *Pichia pastoris*", FEMS Yeast Research, 2007, vol. 7, No. 4, pp. 585-594.
Chauhan et al., "Na,K-ATPase mRNA Levels and Plaque Load in Alzheimer's Disease", Journal of Molecular Neuroscience, 1997, vol. 9, No. 3, pp. 151-166.
Dickey et al., "Dysregulation of Na+/K+ ATPase by amyloid in APP-PS1 transgenic mice", BMC Neuroscience, 2005, vol. 6, No. 1, pp. 1-11.
Japanese Office Action dated Apr. 21, 2015, issued in corresponding Japanese Patent Application No. 2013-551679.
Young et al., "Imaging Correlates of Decreased Axonal $Na^+/K^+$ ATPase in Chronic Multiple Sclerosis Lesions", Annals of Neurology, 2008, vol. 63, No. 4, pp. 428-435.
Mark et al., "Amyloid α-Peptide Impairs Ion-Motive ATPase Activities: Evidence for a Role in Loss of Neuronal $Ca^{2+}$ Homeostasis and Cell Death", The Journal of Neuroscience, 1995, vol. 15, No. 9, pp. 6239-6249.
Ferreiro et al., "An endoplasmic-reticulum-specific apoptotic pathway is involved in prion and amyloid-beta peptides neurotoxicity", Neurobiology of Disease, 2006, vol. 23, No. 3, pp. 669-678.
Hattori et al., "$Cl^-$-ATPase and $Na^+/K^+$-ATPase activities in Alzheimer's disease brains", Neuroscience Letters, 1998, vol. 254, No. 3, pp. 141-144.
Communication pursuant to Article 94(3) EPC issued Jan. 19, 2017, in corresponding European Application No. 12862008.5.
Yu et al., "Intrathecally synthesized IgG in multiple sclerosis cerebrospinal fluid recognizes identical epitopes over time", Journal of Neuroimmunology, 2011, vol. 240-241, pp. 129-136.

\* cited by examiner

Extracellular domain 4                    ASPD binding motif
                                          HLNW              Y-NLWR
NAKa3 (Seq ID 03): F S Y F V I L A E N G F L P G N L V G I R L N W D D R T V N D L E D S Y G Q Q W T Y E Q R K V V E F T C
NAKa1 (Seq ID 04): F T Y F V I L A E N G F L P I H L L G L R V D W D D R W I N D V E D S Y G Q Q W T Y E Q R K I V E F T C
NAKa2 (Seq ID 05): F T Y F V I L A E N G F L P S R L L G I R L D W D D R T M N D L E D S Y G Q E W T Y E Q R K V V E F T C
NAKa4 (Seq ID 06): F T Y F V I L A E N G F R P V D L L G I R L H W E D K Y L N D L E D S Y G Q Q W T Y E Q R K V V E F T C 1 : Primary extract 2 μg
2 : haASD1 IP elute
3 : moIgG IP elute
M : MW markers

NEUROTOXIC TARGET FOR AMYLOSPHEROID, METHOD AND MATERIAL FOR REDUCING THE NEUROTOXICITY OF AMYLOSPHEROID, AND USE THEREOF

CROSS-REFERENCE TO RELATED APPLICATION

This application claims priority to a provisional patent application, Ser. No. 61/581,267, entitled TARGET MOLECULE TO WHICH AMYLOSPHEROID BINDS TO INDUCE DEATH OF MATURE NEURON, METHOD AND SUBSTANCE FOR SUPPRESSING DEATH OF NEURON TRIGGERED BY AMYLOSPHEROID, AND USE THEREOF, filed Dec. 29, 2011, the contents of which are incorporated herein by reference, and to a Japanese patent application, Application No. 2012-2448, entitled TARGET MOLECULE TO WHICH AMYLOSPHEROID BINDS TO INDUCE DEATH OF MATURE NEURON, METHOD AND SUBSTANCE FOR SUPPRESSING DEATH OF NEURON TRIGGERED BY AMYLOSPHEROID, AND USE THEREOF, filed Jan. 10, 2012, the contents of which are incorporated herein by reference.

TECHNICAL FIELD

The disclosure of the present specification relates to a target molecule to which amylospheroid binds to induce death of mature neurons; a method and/or a substance for suppressing death of neurons triggered by amylospheroid; prevention, diagnosis, amelioration, treatment, and/or a pharmaceutical composition for Alzheimer's disease (including Alzheimer-type dementia) and/or dementia with Lewy bodies (Lewy body dementia/diffuse Lewy body disease/cortical Lewy body disease/sentile dementia of Lewy body type); a screening method; an imaging probe; an imaging method; and the like.

BACKGROUND ART

Alzheimer's disease is a disease in which mature neurons die followed by synaptopathy. Owing to the recent research, it is becoming known that the onset of Alzheimer's disease takes place in stages. In a first stage, synaptopathy mainly occurs. This stage is a reversible stage. In a subsequent stage of the reversible stage, neurons die. This stage is an irreversible stage, and it is considered that the onset of Alzheimer's disease takes place when the irreversible stage is reached (Noguchi et al. J. Biol. Chem. vol. 284 no. 47 32895-32905 (2009)).

It is considered that synaptopathy occurs mainly when accumulated β amyloid (Aβ) dimer and dodecamer act on a glutamic acid receptor or the like. However, none of the Aβ dimer and dodecamer causes death of neurons in vitro and in vivo (Shankar et al. Nature Medicine 14, 837-842 (2008)). Therefore, in order to analyze a clinical condition of human Alzheimer's disease, it is necessary to clarify a cause of death of neurons occurring in the irreversible stage after the reversible synaptopathy stage and an underlying molecular mechanism.

Amylospheroid (ASPD) is a unique Aβ assembly that does not exhibit toxicity to non-neuronal cells or immature neurons and that selectively causes death of functionally mature neurons (Noguchi et al. J. Biol. Chem. vol. 284 no. 47 32895-32905 (2009)). Amylospheroid was first isolated as a spherical Aβ assembly having a diameter of about 10 nm causing death of neurons in vitro (Hoshi et al. Pro. Nat'l. Acad. Sci. U.S.A. vol. 100, no. 11, 6370-6375 (2003)). After that, antibodies specific to the synthetic amylospheroid were produced (WO2006/016644 and WO2009/057664), and amylospheroid formed in a living body from the brain of a human patient suffering from Alzheimer's disease (that is, native amylospheroid) was isolated through use of the antibodies (Hoshi et al. Pro. Nat'l. Acad. Sci. U.S.A. vol. 100, no. 11, 6370-6375 (2003)). It was clarified from the research using the native amylospheroid that i) the native amylospheroid selectively induces death of cells with respect to mature neurons in the same way as in the synthetic amylospheroid, ii) the amount of the native amylospheroid in the cerebral cortex of an Alzheimer's disease patient in which neuronal loss is recognized increases relative to the severity of Alzheimer's disease, and in the cerebellum of an Alzheimer's disease patient in which neuronal loss is not so recognized, the native amylospheroid is present merely in a small amount (Hoshi et al. Pro. Nat'l. Acad. Sci. U.S.A. vol. 100, no. 11, 6370-6375 (2003)). Thus, it is considered that amylospheroid plays an important role in the irreversible stage in which the onset of Alzheimer's disease takes place. Further, the native amylospheroid also was detected from the brain of a patient suffering from dementia with Lewy bodies (Noguchi et al. J. Biol. Chem. vol. 284 no. 47 32895-32905 (2009)), and hence, amylospheroid is also considered to play an important role in the onset of dementia with Lewy bodies.

It has been pointed out that amylospheroid, and Aβ dimer and dodecamer which are considered as main causes for synaptopathy, are formed from an Aβ monomer through different paths although they are both Aβ assemblies. That is, the Aβ dimer and dodecamer are formed via the Aβ dimer, whereas amylospheroid is formed from an Aβ trimer (Matsumura et al. J. Biol. Chem. vol. 286 no. 13, 11555-11562 (2011)).

It was predicted that, unlike other Aβ assemblies, amylospheroid binds to the surface of presynaptic cells to induce death of cells with respect to mature neurons (Noguchi et al. J. Biol. Chem. vol. 284 no. 47 32895-32905 (2009)). However, how amylospheroid binds to the mature neurons has remained unclear.

SUMMARY

The present specification discloses a target molecule of amylospheroid, which is expressed in mature neurons, and with which amylospheroid interacts to induce death of cells.

In one or a plurality of aspects, the present disclosure relates to a use of $Na^+/K^+$-ATPase α3 as a binding target molecule of amylospheroid.

DETAILED DESCRIPTION

Figures 1, 2:
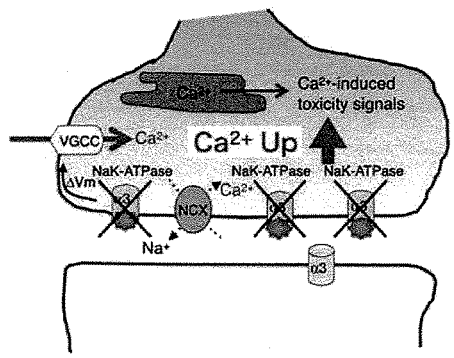
FIG. 1 is an explanatory diagram of a mechanism of death of neurons.
FIG. 2 is a diagram showing a sequence of an extracellular domain 4 of NAK, and parts to which amylospheroid (ASPD) is considered to bind.

In one or a plurality of embodiments, the present disclosure is based on the identification of Na$^+$/K$^+$-ATPase α3 as a target molecule to which amylospheroid binds to act on the surface of mature neurons. Further, in one or a plurality of embodiments, the present disclosure is based on the identification of a polypeptide and/or a peptide motif that has binding ability with respect to amylospheroid and can suppress death of neurons.

In one or a plurality of embodiments, the present disclosure can inhibit death of mature neurons induced by amylospheroid by inhibiting interaction between amylospheroid and Na$^+$/K$^+$-ATPase α3. In one or a plurality of embodiments, the present disclosure preferably enables prevention, amelioration, and/or treatment of Alzheimer's disease and/or dementia with Lewy bodies by inhibiting death of mature neurons induced by amylospheroid. Further, in one or a plurality of embodiments, the present disclosure preferably enables diagnosis of Alzheimer's disease and/or dementia with Lewy bodies based on measurement or imaging of amylospheroid and/or Na$^+$/K$^+$-ATPase α3. Further, in one or a plurality of embodiments, the present disclosure preferably enables a screening method of a compound capable of inhibiting death of mature neurons induced by amylospheroid based on a tertiary structure of a predetermined region of Na$^+$/K$^+$-ATPase α3 to which amylospheroid binds.

Specifically, in one or a plurality of embodiments, the present disclosure can relate to the following:

(1) A use of Na$^+$/K$^+$-ATPase α3 as a target molecule to which amylospheroid binds to induce death of a mature neuron;

(2) A use according to (1), comprising developing a pharmaceutical product based on interaction between the amylospheroid and the Na$^+$/K$^+$-ATPase α3;

(3) A method for suppressing death of a mature neuron induced by amylospheroid, comprising inhibiting protein-protein interaction between the amylospheroid and Na$^+$/K$^+$-ATPase α3;

(4) A method according to (3), wherein the protein-protein interaction between the amylospheroid and the Na$^+$/K$^+$-ATPase α3 is inhibited by contact between the amylospheroid and a substance capable of performing competitive inhibition based on a surface tertiary structure of both or one of the amylospheroid and the Na$^+$/K$^+$-ATPase α3;

(5) A method according to (3), wherein the protein-protein interaction between the amylospheroid and the Na$^+$/K$^+$-ATPase α3 is inhibited by contact between the amylospheroid and a substance capable of binding to the amylospheroid by competition with the Na$^+$/K$^+$-ATPase α3;

(6) A method for suppressing death of a mature neuron induced by amylospheroid, comprising inhibiting at least one calcium channel selected from the group consisting of an N-type voltage-gated calcium channel (VGCC) of a cell membrane, an Na$^+$/Ca$^{2+}$ exchange transporter of mitochondria (mNCX), a membrane-permeable transition pore of mitochondria (mPTP), and a ryanodine receptor of endoplasmic reticulum (RyR), in the mature neuron interacting with the amylospheroid;

(7) A method for preventing, ameliorating, and/or treating Alzheimer's disease and/or dementia with Lewy bodies, comprising suppressing death of a mature neuron induced by amylospheroid by inhibiting protein-protein interaction between the amylospheroid and Na$^+$/K$^+$-ATPase α3;

(8) A method according to (7), wherein the protein-protein interaction between the amylospheroid and the Na$^+$/K$^+$-ATPase α3 is inhibited by contact between the amylospheroid and a substance capable of performing competitive inhibition based on a surface tertiary structure of both or one of the amylospheroid and the Na$^+$/K$^+$-ATPase α3;

(9) A method according to (7), wherein the protein-protein interaction between the amylospheroid and the Na$^+$/K$^+$-ATPase α3 is inhibited by contact between the amylospheroid and a substance capable of binding to the amylospheroid by competition with the Na$^+$/K$^+$-ATPase α3;

(10) A method for preventing, ameliorating, and/or treating Alzheimer's disease and/or dementia with Lewy bodies, comprising inhibiting at least one calcium channel selected from the group consisting of an N-type voltage-gated calcium channel (VGCC) of a cell membrane, an Na$^+$/Ca$^{2+}$ exchange transporter of mitochondria (mNCX), a membrane-permeable transition pore of mitochondria (mPTP), and a ryanodine receptor of endoplasmic reticulum (RyR), in a mature neuron interacting with amylospheroid;

(11) A method for screening a candidate compound of an effective component of a pharmaceutical composition for preventing, ameliorating, and/or treating Alzheimer's disease and/or Lewy body dementia, comprising:

measuring an inhibiting capacity of protein-protein interaction between amylospheroid and $Na^+/K^+$-ATPase α3 through use of a test compound; and selecting the candidate compound based on a result of the measurement;

(12) A method for screening a candidate compound of an effective component of a pharmaceutical composition for preventing, ameliorating, and/or treating Alzheimer's disease and/or dementia with Lewy bodies, comprising:

measuring an inhibiting capacity of protein-protein interaction between amylospheroid and $Na^+/K^+$-ATPase α3, and/or binding ability with respect to the amylospheroid, and/or a suppressive capacity with respect to death of a mature neuron induced by the amylospheroid, using a test compound synthesized by performing Structure-Based Drug Design based on a tertiary structure of an extracellular domain 4 of $Na^+/K^+$-ATPase α3 or a part thereof; and selecting the candidate compound based on a result of the measurement;

(13) A method for diagnosing a clinical condition of Alzheimer's disease and/or dementia with Lewy bodies, comprising:

detecting a signal of an $Na^+/K^+$-ATPase α3 imaging probe including a binding partner of $Na^+/K^+$-ATPase α3 as a binding portion with respect to the $Na^+/K^+$-ATPase α3 from a subject to which the imaging probe has been administered; and determining severity of a clinical condition of Alzheimer's disease and/or dementia with Lewy bodies based on signal data or image data of the signal or a result of measurement of an $Na^+/K^+$-ATPase α3 amount calculated from the signal data or the image data;

(14) A method for checking severity of a clinical condition of Alzheimer's disease and/or dementia with Lewy bodies of a subject, comprising:

detecting a signal of an $Na^+/K^+$-ATPase α3 imaging probe including a binding partner of $Na^+/K^+$-ATPase α3 as a binding portion with respect to the $Na^+/K^+$-ATPase α3 from the subject to which the imaging probe has been administered; and measuring an $Na^+/K^+$-ATPase α3 amount calculated from signal data or image data of the signal; and comparing a result of the measurement with a standard in which the severity is determined to be higher as the measured $Na^+/K^+$-ATPase α3 amount is lower than an $Na^+/K^+$-ATPase α3 amount of a normal individual, and/or the severity is determined to be higher/lower, respectively, in a case where the measured $Na^+/K^+$-ATPase α3 amount is higher/lower than a previous $Na^+/K^+$-ATPase α3 amount of the subject;

(15) A synthesized, isolated, or purified substance that has binding ability with respect to amylospheroid and is capable of suppressing death of a mature neuron induced by the amylospheroid, and that is similar in structure to an extracellular domain 4 of $Na^+/K^+$-ATPase α3 or a part thereof;

(16) A substance according to (15), which is similar in structure to a portion in which an amino acid sequence in the extracellular domain 4 of the $Na^+/K^+$-ATPase α3 is RLNW (SEQ ID NO: 1) or LNW;

(17) A synthesized, isolated, or purified polypeptide, comprising a motif represented by an amino acid sequence of the following Formula (I), (II), or (III):

(I) $X_1X_2X_3X_4$ (SEQ ID NO: 7)

(II) $X_2X_3X_4X_5$ (SEQ ID NO: 43)

(III) $X_2X_3X_4$ (SEQ ID NO 48)

where $X_1$ is arginine (Arg), histidine (His), or lysine (Lys), $X_2$ is a hydrophobic amino acid residue or glycine (Gly), $X_3$ is asparagine (Asn), glutamine (Gln), serine (Ser), threonine (Thr), cysteine (Cys), histidine (His), or tyrosine (Tyr), and $X_4$ is tryptophan (Trp), phenylalanine (Phe), or tyrosine (Tyr), $X_5$ is tryptophan (Trp), tyrosine (Tyr), aspartic acid (Asp), or a hydrophobic amino acid residue, the polypeptide having binding ability with respect to amylospheroid;

(18) A polypeptide according to (17), comprising a motif represented by an amino acid sequence of the Formula (I), (II), or (III) at an N-terminal;

(19) A polypeptide according to (17) or (18), wherein the amino acid sequence has a length of 4 to 25 amino acids;

(20) A polypeptide according to any one of (17) to (19), which is capable of inhibiting interaction between the amylospheroid and $Na^+/K^+$-ATPases α3, and/or suppressing death of a mature cell induced by the amylospheroid;

(21) A polypeptide according to any one of (17) to (20), which is similar in structure to an extracellular domain 4 of $Na^+/K^+$-ATPase α3 or a part thereof;

(22) A polypeptide according to (21), which is similar in structure to a portion in which an amino acid sequence in the extracellular domain 4 of the $Na^+/K^+$-ATPase α3 is RLNW (SEQ ID NO: 1);

(23) A peptide mimetic similar in structure to the polypeptide according to any one of (17) to (22), which is capable of inhibiting interaction between the amylospheroid and $Na^+/K^+$-ATPases α3, and/or suppressing death of a mature neuron induced by the amylospheroid;

(24) A polynucleotide encoding the polypeptide according to any one of (17) to (22);

(25) A vector for expressing the polypeptide according to any one of (17) to (22), comprising a polynucleotide encoding the polypeptide;

(26) A composition comprising the polypeptide according to any one of (17) to (22) or the peptide mimetic according to (23);

(27) A composition according to (26), used for detecting and/or measuring the amylospheroid;

(28) A composition according to (26), used for suppressing death of a mature neuron induced by the amylospheroid;

(29) A composition according to (26), used for inhibiting interaction between the amylospheroid and $Na^+/K^+$-ATPase α3;

(30) A pharmaceutical composition comprising the polypeptide according to any one of (17) to (22), the peptide mimetic according to (23), the polynucleotide according to (24), or the vector according to (25);

(31) A pharmaceutical composition according to (30), used for preventing, ameliorating, and/or treating Alzheimer's disease and/or dementia with Lewy bodies;

(32) A probe with respect to amylospheroid or a precursor thereof, comprising the polypeptide according to any one of (17) to (22) or the peptide mimetic according to (23) as a binding portion with respect to the amylospheroid;

(33) A probe or a precursor thereof according to (32), used for imaging the amylospheroid, or detecting or measuring the amylospheroid;

(34) An amylospheroid imaging method, comprising detecting a signal of an amylospheroid imaging probe including the polypeptide according to any one of (17) to (22) or the peptide mimetic according to (23) as a binding portion with respect to the amylospheroid from a subject to which the imaging probe has been administered;

(35) A method for measuring an amylospheroid amount, comprising calculating an amylospheroid amount based on signal data or image data obtained by the amylospheroid imaging method according to (34);

(36) A diagnosis method for diagnosing a clinical condition of Alzheimer's disease and/or dementia with Lewy bodies, comprising:

detecting a signal of an amylospheroid imaging probe including a binding partner of amylospheroid as a binding portion with respect to the amylospheroid from a subject to which the imaging probe has been administered; and determining severity of a clinical condition of Alzheimer's disease and/or dementia with Lewy bodies based on signal data or image data of the signal, or a result of measurement of an amylospheroid amount calculated from the signal data or the image data;

(37) A diagnosis method according to (36), wherein the binding partner of the amylospheroid is the polypeptide according to any one of (17) to (22) or the peptide mimetic according to (23);

(38) A method for checking severity of a clinical condition of Alzheimer's disease and/or dementia with Lewy bodies of a subject, comprising:

detecting a signal of an amylospheroid imaging probe including a binding partner of amylospheroid as a binding portion with respect to the amylospheroid from a subject to which the imaging probe has been administered;

measuring an amylospheroid amount calculated from signal data or image data of the signal; and comparing a result of the measurement with a standard in which the severity is determined to be higher as the calculated amylospheroid amount is lower than an amylospheroid amount of a normal individual, and/or the severity is determined to be higher/lower, respectively, in a case where the calculated amylospheroid amount is higher/lower than a previous amylospheroid amount of the subject;

(39) A method according to (38), wherein the binding partner of the amylospheroid is the polypeptide according to any one of (17) to (22) or the peptide mimetic according to (23).

[Amylospheroid]

In the present specification, amylospheroid (hereinafter, sometimes referred to as "ASPD") refers to an Aβ assembly capable of selectively inducing death of cells with respect to functionally mature neurons. ASPD includes "synthetic ASPD" and "native ASPD". The synthetic ASPD refers to ASPD that is a spherical structure having a diameter of about 10 to 15 nm, prepared and isolated in vitro through use of synthetic Aβ (Hoshi et al. Pro. Nat'l. Acad. Sci. U.S.A. vol. 100, no. 11, 6370-6375 (2003)). Further, the native ASPD refers to ASPD formed in a human living body, above all, ASPD that can be isolated from the brain of a patient suffering from Alzheimer's disease and/or dementia with Lewy bodies (Noguchi et al. J. Biol. Chem. vol. 284 no. 47 32895-32905 (2009)). The synthetic ASPD and the native ASPD both induce death of cells with respect to mature human neurons. Anti-ASPD antibodies capable of recognizing a tertiary structure specific to ASPD also were produced (for example, haASD1, haASD2, mASD3, etc., disclosed by WO2006/016644 and WO2009/057664). From results of characteristics analysis of anti-ASPD monoclonal antibodies and NMR analysis of ASPD, it has been known that ASPD has a unique tertiary structure different from those of other Aβ assemblies reported so far (for example, Supplemental Table S1 of Noguchi et al. J. Biol. Chem. vol. 284 no. 47 32895-32905 (2009), report in 2010 of Health and Labour Sciences Research Grant (Medical equipment development research promotion business)). Specifically, first, it is known from a result of an epitope map of the anti-ASPD antibodies that, Aβ is folded in ASPD, and an N-terminal and a middle portion of Aβ are present on the surface of ASPD. From this, it is understood that a three-dimensional surface structure specific to ASPD is formed. A two-dimensional NMR spectrum of ASPD also supports this result. Of signals to be originally detected with an Aβ monomer, a signal can be observed in a site present on the surface of ASPD. On the other hand, a signal derived from a site folded inside ASPD is not equivalent magnetically and has its mobility suppressed by being folded inside, and hence, the signal attenuates and cannot be detected. The result obtained from the NMR analysis also shows that the N-terminal and the intermediate site of Aβ are exposed to the surface of ASPD, which was matched with a site to be recognized by the anti-ASPD antibodies. The intermediate site present on the surface of ASPD is a site folded inside when it is in the form of an ordinary aggregate, and is shown to be an aggregate having a specific tertiary structure of ASPD. Accordingly, in the present specification, ASPD also can be referred to as an Aβ assembly capable of reacting with anti-ASPD antibodies specific to ASPD disclosed by WO2006/016644 and WO2009/057664 and selectively inducing death of cells with respect to functionally mature neurons. In one or a plurality of non-limiting embodiments, ASPD is about 20 to 150-mers of an Aβ monomer. In one or a plurality of non-limiting embodiments, ASPD has a molecular weight of about 84 kDa to about 172 kDa, and an average molecular weight of about 128 kDa as a form having high cytotoxicity. In one or a plurality of non-limiting embodiments, ASPD has a diameter of about 4.6 nm to about 9.8 nm (average: about 7.2 nm) as measured by an atomic force microscope (AFM) in a solution.

The synthetic ASPD can be prepared by a method disclosed by Hoshi et al. Pro. Nat'l. Acad. Sci. U.S.A. vol. 100, no. 11, 6370-6375 (2003). Specifically, the synthetic ASPD can be formed by slowly rotating and agitating a synthesized amyloid β monomer ($A\beta_{1-40}$ and/or $A\beta_{1-42}$) for 5 to 7 days ($A\beta_{1-40}$) or overnight ($A\beta_{1-42}$), and the synthetic ASPD can be purified by collecting a retentate obtained by subjecting a 0.22 μm-filter filtrate to 50 kDa or 100 kDa ultrafiltration. Note that, in the present specification, the synthetic ASPD is not limit to those which are produced by this production method. As an Aβ monomer used for the synthetic ASPD, those of humans or animals other than humans can be used. On the other hand, the native ASPD can be obtained by a method disclosed by Noguchi et al. J. Biol. Chem. vol. 284 no. 47 32895-32905 (2009). Specifically, the native ASPD can be obtained by performing immunoprecipitation with respect to a retentate obtained by subjecting a brain extract of a patient suffering from Alzheimer's disease or the like to 100 kDa ultrafiltration, through use of monoclonal antibodies specific to an ASPD tertiary structure such as haASD1, haASD2, or mASD3 disclosed by WO2006/016644 and WO2009/057664. Note that, in the present specification, the native ASPD is not limited to those which are obtained by this production method.

[Amyloid β Peptide]

In the present specification, the term "amyloid β monomer" refers to a peptide to be cleaved when an amyloid precursor protein (APP) is cleaved with β- and γ-serectase, and also is denoted as "β amyloid", "Aβ", or "Aβ monomer". Further, in the present specification, Aβ can include those which are called $A\beta_{1-39}$, $A\beta_{1-40}$, $A\beta_{1-41}$, $A\beta_{1-42}$, and $A\beta_{1-43}$ due to a length of an amino acid sequence thereof. In the present specification, Aβ may be a human type (sequence present in humans) or a non-human type (sequence present in animals other than humans). Further, in the present specification, Aβ can include (native) Aβ in a living body and synthesized Aβ. Although not limited, the synthetic Aβ can be synthesized by a known peptide synthesis method (for example, an Fmoc method or a Boc method), and can be produced, for example, using a known peptide synthesizer. The human-type $A\beta_{1-42}$ (also called "Aβ42") is a peptide formed of an amino acid sequence represented by an amino acid sequence (from an N-terminal): DAEFRHDSGYEVH-HQKLVFFAEDVGSNKGAIIGLMVGGVVIA (SEQ ID NO: 2). Further, the human-type $A\beta_{1-41}$ (Aβ41), $A\beta_{1-40}$ (Aβ40), and $A\beta_{1-39}$ (Aβ39) are peptides formed of amino acid sequences lacking A, IA, and VIA, respectively, from a C-terminal of an amino acid sequence of SEQ ID NO: 2. Further, the human-type $A\beta_{1-43}$ (Aβ43) is a peptide formed of an amino acid sequence in which one threonine residue (T/Thr) is added to a C-terminal of the amino acid sequence of SEQ ID NO: 2.

[$Na^+/K^+$-ATPase α3]

In the present specification, $Na^+/K^+$-ATPase α3 (hereinafter, also referred to as "NAKα3") refers to "sodium/potassium transporter ATPase subunit α3" that is a membrane protein of a gene product of an ATP1A3 gene. $Na^+/K^+$ATPase is an ATPase transporter that serves to keep an electrochemical gradient of sodium and potassium via a cytoplasmic membrane. α3 is considered to participate in keeping a membrane potential, particularly, in neurons. In the present specification, the ATP1A3 gene and NAKα3 may be a human type (sequence present in humans) or a non-human type (sequence present in animals other than humans). In the present specification, the term "animals other than humans" includes but is not particularly limited to animals having cells expressing Ortholog of human Aβ and/or human NAKα3, and in one or a plurality of embodiments, examples thereof include mammals such as primates and rodents (e.g., a monkey and a rat).

The human ATP1A3 gene can be determined by NCBI database accession No. NM_152296.3 (mRNA, dated May 12, 2011). Further, human NAKα3 can be determined by Accession No. NP_689509.1 (mRNA, dated May 12, 2011).

[Identification of NAKα3 that is a Target Molecule of ASPD]

NAKα3 is a target molecule to which ASPD binds to induce death of cells with respect to mature neurons. In the present specification, the "target molecule of ASPD" includes a "target molecule to which ASPD binds to induce death of cells with respect to mature neurons". NAKα3 that is a target molecule of ASPD was identified as follows. That is, extracts derived from mature neurons, immature neurons, and HEK 293 cells that were cells derived from the human fetus kidney were respectively developed by electrophoresis and detected using ASPD formed in a living body (that is, native ASPD) as a ligand and using anti-ASPD antibodies, whereby far-western blotting was performed. As a result, NAKα3 was identified from a band of about 105 kDa appearing only in the case of mature neurons. Although the band is detected even in the case of using the synthetic ASPD as a ligand, the band does not appear in far-western blotting using an Aβ monomer as a ligand and using anti-Aβ antibodies (6E10) for detection. Further, when a cell extract of mature hippocampal neurons (21 DIV) of a rat is subjected to immunoprecipitation with anti-ASPD antibodies in the coexistence of ASPD, NAKα3 is coprecipitated.

There are four $Na^+/K^+$ATPase α subunits: α1 to α4. Of those, mainly, α1 and α3 are expressed in neurons. α1 is generally expressed in all cells including the mature neurons, immature neurons, and HEK293 cells. On the other hand, α3 is expressed only in mature neurons. In the hippocampus or the like that is damaged easily by Alzheimer's disease, the mRNA expression amount of α3 is twice to three times or more of that of α1. Thus, the selective inducement of death of cells by ASPD with respect to mature neurons can be explained by the fact that a target molecule is $Na^+/K^+$-ATPase α3 (NAKα3).

[Mechanism of Death of Cells in Mature Neurons Induced by ASPD]

A mechanism in which ASPD is subjected to protein-protein interaction with NAKα3 that is a target to induce death of cells with respect to mature neurons is considered as follows. When ASPD interacts with NAKα3, the function of $Na^+/K^+$ATPase of mature neurons is inhibited. Therefore, a cell membrane potential increases and neurons take a hyperexcitable state, and a large amount of extracellular $Ca^{2+}$ flowed into cells through a voltage-gated calcium channel. It is considered that intracellular $Ca^{2+}$ homeostasis is lost due to the extraordinary flow of $Ca^{2+}$, and as a result, an intracellular $Ca^{2+}$ concentration increases excessively to cause death of cells (see FIG. 1). More specifically, it is considered that the increase in intracellular $Ca^{2+}$ concentration causes activation of calpain, activation of p25/cyclin-dependent kinase 5 (CDK5), activation of glycogen synthase kinase-3β (GKS3β), and excessive phosphorylation of tau protein in this order to cause death of cells with respect to mature neurons. It should not be interpreted that the present disclosure is limited to these mechanisms.

[Protein-Protein Interaction Between ASPD and NAKα3]

It is an unreported new finding beyond the prediction of prior art that death of mature neurons induced by ASPD is caused by protein-protein interaction between ASPD and NAKα3. If protein-protein interaction between ASPD and NAKα3 can be inhibited, death of mature neurons induced by ASPD can be suppressed, and in addition, this enables treatment, diagnosis, amelioration, and/or prevention of Alzheimer's disease and/or dementia with Lewy bodies. Thus, in one or plurality of embodiments, the present disclosure relates to a use of NAKα3 as a target molecule to which amylospheroid binds to induce death of mature neurons. In one or a plurality of embodiments, the use of NAKα3 as the target molecule of ASPD may include suppressing death of neurons of ASPD by inhibiting the protein-protein interaction between ASPD and NAKα3, treating, diagnosing, ameliorating, and/or preventing Alzheimer's disease and/or dementia with Lewy bodies by inhibiting the protein-protein interaction between ASPD and NAKα3, and developing a medical composition based on the interaction between ASPD and NAKα3. In one or a plurality of embodiments, the use of NAKα3 as the target molecule of ASPD may include the invention disclosed in the present specification and embodiments thereof. In the present specification, the term "protein-protein interaction" includes binding, and the term "protein-protein interaction between ASPD and NAKα3" includes allowing an action capable of eventually causing death of cells to influence NAKα3. Further, in the present specification, the term "Alzheimer's disease" includes Alzheimer-type dementia. Further, in the present specification, targets of "treatment, diagnosis, amelioration, and/or prevention of Alzheimer's disease and/or dementia with Lewy bodies" can include but are not particularly limited to humans and/or animals other than humans.

Thus, in one or a plurality of embodiments, the present disclosure relates to a method for suppressing death of mature neurons induced by ASPD, including inhibiting the protein-protein interaction between ASPD and NAKα3. In one or a plurality of embodiments, the present disclosure also relates to a method for preventing, ameliorating, and/or treating Alzheimer's disease and/or dementia with Lewy bodies, including suppressing death of mature neurons induced by ASPD by inhibiting the protein-protein interaction between ASPD and NAKα3.

[Method for Inhibiting Protein-Protein Interaction Between ASPD and NAKα3]

As described above, ASPD is an Aβ assembly having a unique tertiary structure. Therefore, a substance (for example, a polypeptide, a peptide mimetic, a low molecular weight compound, a salt thereof, a solvate thereof, etc.) which mimics a tertiary structure of a site of ASPD or NAKα3 participating in the protein-protein interaction between ASPD and NAKα3 would be able to inhibit the protein-protein interaction between ASPD and NAKα3. Although it is considered that the presence of molecules mimicking a tertiary structure of one of the sites that are to interact with each other causes competitive inhibition, the present disclosure may not be limited to this way of thinking. In the present specification, the term "substance" can refer to a compound, a salt thereof, a salvate thereof, and/or a composition containing them, and more specifically, can refer to a polypeptide, a peptide mimetic, a low molecular weight compound, a salt thereof, a salvate thereof, and/or a composition containing them.

Thus, in one or a plurality of embodiments, the method for inhibiting the protein-protein interaction between ASPD and NAKα3 in the present disclosure relates to a method including causing ASPD or NAKα3 and a substance mimicking a tertiary structure of a site of ASPD or NAKα3 participating in the interaction between ASPD and NAKα3 to interact with each other. Further, in one or a plurality of embodiments, a method for inhibiting the protein-protein interaction between ASPD and NAKα3 in the present disclosure relates to a method to be conducted by the contact between ASPD and a substance capable of performing competitive inhibition based on a surface tertiary structure of both or one of ASPD and NAKα3. Further, in one or a plurality of embodiments, a method for inhibiting the protein-protein interaction between ASPD and NAKα3 in the present disclosure relates to a method to be conducted by the contact between ASPD and a substance capable of binding to ASPD by competition with NAKα3. These methods for inhibiting the protein-protein interaction between ASPD and NAKα3 can be applied to the above-mentioned method for suppressing death of mature neurons induced by ASPD and the above-mentioned method for preventing, ameliorating, and/or treating Alzheimer's disease and/or dementia with Lewy bodies.

ASPD interacts mainly with an extracellular domain 4 of NAKα3. The extracellular domain 4 of human NAKα3 is presumed to be a 857 to 908th sequence (SEQ ID NO: 3, FIG. 2) of an amino acid sequence of ACNo. NP_689509.1. FIG. 2 is a diagram showing an example of two motifs (motifs interacting with ASPD; hereinafter, sometimes referred to as "ASPD interacting motifs"), which were newly found based on a polypeptide (AAP peptide) shown in examples, as shaded areas, in which extracellular domains 4 (SEQ ID NO: 3-6) in human NAKα1 to NAKα4 are aligned. Further, partial sequences of an AAT01 peptide (SEQ ID NO: 35) shown in the examples are aligned above the two ASPD interacting motifs in FIG. 2. Of the two ASPD interacting motifs in FIG. 2, the ASPD interacting motif on an N-terminal side including "RLNW" or "LNW" of NAKα3 is a portion in which NAKα3 has a sequence and structure different from those of the other NAKα's (FIG. 2), and this portion is considered to be important due to the specific protein-protein interaction between ASPD and NAKα3. In a portion including a motif ("Y-NLWR" in the AAT01 peptide) on a C-terminal side including "YGQQWT" of NAKα3, NAKα3 and NAKα1 have a sequence structure in common. The extracellular domain 4 of NAKα3 is completely stored in a human and a rat (not shown).

Thus, in one or a plurality of embodiments, a method for inhibiting the protein-protein interaction between ASPD and NAKα3 in the present disclosure can be conducted using a substance mimicking a tertiary structure of the extracellular domain 4 of NAKα3, the portion including "RLNW" or "LNW" and/or the portion including "YGQQWT" or "Y-NLWR", or a substance capable of performing competitive inhibition based on the tertiary structure. These substances also can be obtained by performing Structure-Based Drug Design (SBDD) based on the extracellular domain 4 of NAKα3, the portion including "RLNW" or "LNW", and/or the portion including "YGQQWT" or "Y-NLWR". As described above, the method for inhibiting the protein-protein interaction between ASPD and NAKα3 can be applied to the above-mentioned method for suppressing death of mature neurons induced by ASPD and the above-mentioned method for preventing, ameliorating, and/or treating Alzheimer's disease and/or dementia with Lewy bodies. The extracellular domain 4 of NAKα3 is known to be a site that directly interacts with an NAKβ subunit, and it is considered that the interaction of the extracellular domain 4 with the NAKβ subunit influences structural stability and enzyme activity.

In one or a plurality of embodiments, the present disclosure relates to a synthesized, isolated, or purified substance, which has binding ability with respect to ASPD, and is capable of suppressing death of mature neurons induced by ASPD and is similar in structure to the extracellular domain 4 of NAKα3 or a part thereof. The substance relates to a polypeptide, a peptide mimetic, a low molecular weight compound, a salt thereof, a salvate thereof, and/or a composition containing them. In one or a plurality of embodiments, the tertiary structure of the extracellular domain 4 of NAKα3 or a part thereof is a tertiary structure of the extracellular domain 4 of NAKα3, the portion including "RLNW" or "LNW", and/or the portion including "YGQQWT" or "Y-NLWR". In one or a plurality of embodiments, these substances can be used for inhibiting the interaction between ASPD and NAKα3, suppressing death of mature neurons induced by ASPD, or preventing, ameliorating, diagnosing, and/or treating Alzheimer's disease and/or dementia with Lewy bodies.

In the present specification, the term "peptide mimetic" includes a peptide-like compound (e.g., peptoid) and other variants known in the field. Specifically, examples thereof include peptoid (S. M. Miller, R. J. Simon, S. Ng, R. N. Zuckermann, J. S. Kerr, W. H. Moos, Bioorg. Med. Chem Lett., 4, 2657 (1994)) which is a known N-substituted glycine oligomer, or a non-peptide compound (M. Kahn Tetrahedron, 49, 3433 (1993), Combinatorial Chemistry, Kagaku-Dojin Publishing Company, INC. p. 44-64, 1997) mimicking a β, γ turn structure of a protein. In the present specification, the term "low molecular weight compound" refers to a compound having a molecular weight of, for example, 700 or less, preferably 500 or less.

[Anti-NAKα3 Antibody]

Still further, in one or a plurality of embodiments, the present disclosure relates to anti-NAKα3 antibodies that specifically recognize a tertiary structure of the extracellular domain 4 of NAKα3, the portion including "RLNW" or "LNW", and/or the portion including "YGQQWT" or "Y-NLWR". In one or a plurality of embodiments, the anti-NAKα antibodies are polyclonal antibodies, monoclonal antibodies, humanized antibodies, and/or fully human antibodies. Of those antibodies, in one or a plurality of embodiments, the antibodies that do not inhibit the function of an ion channel of NAKα3 while inhibiting the interaction between NAKα3 and ASPD are preferred. Thus, in one or a plurality of embodiments, the present disclosure relates to a method for suppressing death of mature neurons induced by ASPD and a method for preventing, ameliorating, and/or treating Alzheimer's disease and/or dementia with Lewy bodies, including causing the anti-NAKα3 antibodies to bind to NAKα3 of mature neurons under the condition that amylospheroid may be present. Further, in another aspect, the present disclosure relates to a composition containing the anti-NAKα3 antibodies to be used in a method for suppressing death of mature neurons induced by ASPD or a method for preventing, ameliorating, and/or treating Alzheimer's disease and/or dementia with Lewy bodies.

[Screening Method]

In one or a plurality of embodiments, the present disclosure relates to a screening method of a candidate compound of an effective component of a pharmaceutical composition for preventing, ameliorating, and/or treating Alzheimer's disease and/or dementia with Lewy bodies, including measuring an inhibiting capacity of the protein-protein interaction between ASPD and NAKα3 using a test compound and selecting a candidate compound based on a result of the measurement.

Further, in one or a plurality of embodiments, the present disclosure relates to a screening method of a candidate compound of an effective component of a pharmaceutical composition for preventing, ameliorating, and/or treating Alzheimer's disease and/or dementia with Lewy bodies, including measuring an inhibiting capacity of the protein-protein interaction between amylospheroid and $Na^+/K^+$-ATPase α3, and/or binding ability with respect to amylospheroid, and/or a suppressive capacity with respect to death of mature neurons induced by amylospheroid, using a test compound synthesized by performing Structure-Based Drug Design (SBDD) based on a tertiary structure of the extracellular domain 4 of NAKα3 or a part thereof and selecting a candidate compound based on a result of the measurement. In one or a plurality of embodiments, a tertiary structure of the extracellular domain 4 of NAKα3 or a part thereof is a tertiary structure of the extracellular domain 4 of NAKα3, the portion including "RLNW" or "LNW", and/or the portion including "YGQQWT" or "Y-NLWR".

[Suppression of Death of Cells by Calcium Channel Inhibitor]

An N-type voltage-gated calcium channel (VGCC) causes $Ca^{2+}$ to flow into cells from outside thereof due to the interaction between ASPD and NAKα3 to cause death of the nerve. Further, it is considered that the flow of $Ca^{2+}$ from the cell organelle to the cytoplasm also participates in death of cells. Thus, in anther aspect, the present disclosure relates to a method for suppressing death of mature neurons induced by ASPD and a method for preventing, ameliorating, and/or treating Alzheimer's disease and/or dementia with Lewy bodies, including inhibiting at least one calcium channel selected from the group consisting of an N-type voltage-gated calcium channel (VGCC) of a cell membrane, an $Na^+/Ca^{2+}$ exchange transporter of mitochondria (mNCX), membrane-permeable transition pore of mitochondria (mPTP), and a ryanodine receptor of the endoplasmic reticulum (RyR), in mature neurons treated with amylospheroid. As an inhibitor of each calcium channel, a known inhibitor may be used. Further, in another aspect, the present disclosure relates to a composition or a pharmaceutical composition containing a compound capable of inhibiting at least one calcium channel selected from the group consisting of an N-type voltage-gated calcium channel (VGCC) of the cytoplasm, an $Na^+/Ca^{2+}$ exchange transporter of mitochondria (mNCX), membrane-permeable transition pore of mitochondria (mPTP), and a ryanodine receptor of the endoplasmic reticulum (RyR), used for a method for suppressing death of mature neurons induced by ASPD or a method for preventing, ameliorating, and/or treating Alzheimer's disease and/or dementia with Lewy bodies.

[ASPD Interacting Motif]

The ASPD interacting motif (motif interacting with ASPD) can be represented by an amino acid sequence of the following Formula (I), (II), or (III).

(I)
$X_1X_2X_3X_4$
(SEQ ID NO: 7)

(II)
$X_2X_3X_4X_5$
(SEQ ID NO: 43)

(III)
$X_2X_3X_4$
(SEQ ID NO: 48)

where $X_1$ is arginine (Arg), histidine (His), or lysine (Lys),
$X_2$ is a hydrophobic amino acid residue or glycine (Gly),
$X_3$ is asparagine (Asn), glutamine (Gln), serine (Ser), threonine (Thr), cysteine (Cys), histidine (His), or Tyr (tyrosine),
$X_4$ is tryptophan (Trp), phenylalanine (Phe), or tyrosine (Tyr), and
$X_5$ is tryptophan (Trp), tyrosine (Tyr), aspartic acid (Asp), or a hydrophobic amino acid residue.

In the present specification, the hydrophobic amino acid residue includes leucine (Leu), valine (Val), isoleucine (Ile), phenylalanine (Phe), proline (Pro), alanine (Ala), and methionine (Met).

In one or a plurality of embodiments, it is preferred that $X_1$ be histidine or arginine in the ASPD interacting motif from the viewpoint of enhancing the interaction with ASPD. In one or a plurality of embodiments, from the same viewpoint, $X_2$ is preferably a hydrophobic amino acid residue, more preferably leucine, isoleucine, valine, and phenylalanine, still more preferably leucine, isoleucine, and phenylalanine, and still further preferably leucine and phenylalanine. In one or a plurality of embodiments, from the same viewpoint, $X_3$ is preferably asparagine, glutamine, histidine, and more preferably asparagine. In one or a plurality of embodiments, from the same viewpoint, $X_4$ is preferably tryptophan. $X_5$ is preferably tryptophan, phenylalanine, tyrosine, or aspartic acid, from the same viewpoint.

In one or a plurality of embodiments, it is preferred that, in the ASPD interacting motif, a seventh or eighth amino acid residue (that is, 2nd to 4th amino acid residues from $X_4$ to a C-terminal) (if any) be tryptophan from the viewpoint of strengthening the interaction with ASPD.

In one or a plurality of embodiments, a length of the ASPD interacting motif is preferably 3 to 25 amino acids or 4 to 25 amino acids, more preferably 3 to 20 amino acids or 4 to 20 amino acids, still more preferably 3 to 18 amino acids or 4 to 18 amino acids, still further preferably 3 to 14 amino acids or 4 to 14 amino acids, still further preferably 3 to 12 amino acids, 4 to 12 amino acids, or 5 to 12 amino acids, still further preferably 3 to 8 amino acids or 4 to 8 amino acids from the viewpoint of enhancing the interaction with ASPD.

In one or a plurality of embodiments, examples of the ASPD interacting motif include motifs represented by the following amino acid sequences (SEQ ID NO: 7 to 34, 42 to 51).

$X_1X_2X_3X_4$ (SEQ ID NO: 7)

$X_1X_2NW$ (SEQ ID NO: 8)

$HX_2NW$ (SEQ ID NO: 9)

$H(F/L)NW$ (SEQ ID NO: 10)

HFNW (SEQ ID NO: 42)

$X_2X_3X_4X_5$ (SEQ ID NO: 43)

$X_2NWX_5$ (SEQ ID NO: 44)

$(F/L)NWX_5$ (SEQ ID NO: 45)

$(F/L)NWD$ (SEQ ID NO: 46)

FNWD (SEQ ID NO: 47)

$X_2X_3X_4$ (SEQ ID NO: 48)

$X_2NW$ (SEQ ID NO: 49)

$(F/L)NW$ (SEQ ID NO: 50)

FNW (SEQ ID NO: 51)

$X_1X_2X_3X_4X_5$ (SEQ ID NO: 11)

$X_1X_2NWX_5$ (SEQ ID NO: 12)

$HX_2NWX_5$ (SEQ ID NO: 13)

$H(F/L)NWX_5$ (SEQ ID NO: 14)

$H(F/L)NWY$ (SEQ ID NO: 15)

$H(F/L)NWW$ (SEQ ID NO: 16)

$H(F/L)NWL$ (SEQ ID NO: 17)

$H(F/L)NWD$ (SEQ ID NO: 18)

$X_1X_2NWX_5W$ (SEQ ID NO: 19)

$HX_2NWX_5W$ (SEQ ID NO: 20)

$H(F/L)NWX_5W$ (SEQ ID NO: 21)

$H(F/L)NWYW$ (SEQ ID NO: 22)

$H(F/L)NWWW$ (SEQ ID NO: 23)

$H(F/L)NWLW$ (SEQ ID NO: 24)

$H(F/L)NWDW$ (SEQ ID NO: 25)

$X_1X_2NWX_5XW$ (SEQ ID NO: 26)

$HX_2NWX_5XW$ (SEQ ID NO: 27)

$H(F/L)NWX_5XW$ (SEQ ID NO: 28)

$X_1X_2NWX_5XXW$ (SEQ ID NO: 29)

$HX_2NWX_5XXW$ (SEQ ID NO: 30)

$H(F/L)NWX_5XXW$ (SEQ ID NO: 31)

$H(F/L)NWYNLW$ (SEQ ID NO: 32)

$H(F/L)NWWHSW$ (SEQ ID NO: 33)

$H(F/L)NWLSWF$ (SEQ ID NO: 34)

In amino acid sequences of SEQ ID NO: 7 to 34, 42 to 51, $X_1$ to $X_5$ are as described above, and X is any amino acid residue.

[Polypeptide]

In one or a plurality of embodiments, the present disclosure relates to a synthesized, isolated, or purified polypeptide (hereinafter, sometimes referred to as "first polypeptide") including the above-mentioned ASPD interacting motif and having binding ability with respect to amylospheroid. In the first polypeptide, an embodiment of the above-mentioned ASPD interacting motif is as described above. In one or a plurality of embodiments, the first polypeptide preferably can suppress death of mature neurons induced by ASPD, more preferably can further/alternatively inhibit the interaction between ASPD and NAKα3.

From the viewpoint of enhancing the inhibition of ASPD-NAKα3 interaction, it is preferred that the first polypeptide have the above-mentioned ASPD interacting motif at an N-terminal, that is, a first amino acid at the N-terminal be $X_1$ or $X_2$. The length of the first polypeptide is not particularly limited as long as it is a length including the above-mentioned Formula (I). The first polypeptide may be formed of the ASPD interacting motif or further include an amino acid sequence in addition to the ASPD interacting motif. In one or a plurality of embodiments, the length of the first polypeptide is 50 or less, 25 or less, 20 or less, or 15 or less, and/or 3 or more, 4 or more, 5 or more, 6 or more, 9 or more, or 10 or more from the viewpoint of enhancing the suppression of ASPD-induced death of mature neurons and/or the inhibition of the ASPD-NaKα3 interaction.

In another aspect, the present disclosure relates to a synthesized, isolated, or purified second polypeptide having binding ability with respect to amylospheroid and being capable of suppressing death of mature neurons induced by amylospheroid. It is preferred that the second polypeptide of the present disclosure mimic a tertiary structure of the extracellular domain 4 of NAKα3 or a part thereof, preferably a tertiary structure of the extracellular domain 4 of NAKα3, the portion including "RLNW" or "LNW", and/or the portion including "YGQQWT" or "Y-NLWR", and further/alternatively, it is more preferred that the second polypeptide can inhibit the interaction between ASPD and NAKα3. As one embodiment of the second polypeptide, there is the first polypeptide. The length of the second polypeptide is not particularly limited and can be set to be equal to that of the first polypeptide of the present disclosure.

In one or a plurality of embodiments, as the polypeptide (including the first and second polypeptides, which is similarly applies hereinafter) of the present disclosure, there is a form in which the ASPD interacting motif and a brain-migrating peptide bind to each other directly or through a linker peptide. By causing the brain-migrating peptide to bind to the ASPD interacting motif, efficiency at which the polypeptide of the present disclosure migrates to the brain beyond the blood-brain barrier can be enhanced. As the brain-migrating peptide, those which are conventionally known can be used.

The polypeptide of the present disclosure can be prepared by appropriate synthesis according to an ordinary synthesis method and purification. It is preferred that the polypeptide of the present disclosure have a synthesized, isolated, and/or purified form.

By allowing the polypeptide of the present disclosure to coexist with ASPD or bringing the polypeptide into contact with ASPD, the polypeptide of the present disclosure binds to ASPD. Thus, the polypeptide of the present disclosure can be used preferably for suppressing death of mature neurons induced by ASPD and/or inhibiting the interaction between ASPD and NAKα3, and the polypeptide can be used in a method for preventing, ameliorating, and/or treating Alzheimer's disease and/or dementia with Lewy bodies, as an effective component for a pharmaceutical composition. Accordingly, in another aspect, the present disclosure relates to a pharmaceutical composition containing the polypeptide of the present disclosure, used in a method for preventing, ameliorating, and/or treating Alzheimer's disease and/or dementia with Lewy bodies.

Alternatively, the polypeptide of the present disclosure can be used as a probe of ASPD or an imaging probe or a precursor thereof, and can be used in a method for detecting and/or measuring ASPD, an ASPD imaging method, and a method for determining and/or diagnosing severity of a clinical condition of Alzheimer's disease and/or dementia with Lewy bodies. Thus, in another aspect, the present disclosure relates to a composition, a pharmaceutical composition, or a kit including the polypeptide of the present disclosure, for detecting and/or measuring ASPD, for imaging ASPD, or for determining and/or diagnosing severity of a clinical condition of Alzheimer's disease and/or dementia with Lewy bodies.

[Peptide Mimetic]

As still another aspect, the present disclosure relates to a peptide mimetic that mimics a structure of the polypeptide of the present disclosure. The peptide mimetic of the present disclosure has an inhibiting capacity with respect to the interaction between ASPD and NAKα3. As a preferred embodiment of the peptide mimetic of the present disclosure, there is a form in which a peptide mimetic of a motif represented by the Formula (I) and the brain-migrating peptide bind to each other directly or through a linker. By causing the brain-migrating peptide to bind to the peptide mimetic, efficiency at which the peptide mimetic of the present disclosure migrates to the brain beyond the blood-brain barrier can be enhanced. As the brain-migrating peptide, those which are conventionally known can be used.

By allowing the peptide mimetic of the present disclosure to coexist with ASPD or bringing the peptide mimetic into contact with ASPD, the interaction between ASPD and NAKα3 is inhibited. Thus, the peptide mimetic of the present disclosure preferably can be used for suppressing death of mature neurons induced by ASPD and/or inhibiting the interaction between ASPD and NAKα3, and can be used in a method for preventing, ameliorating, and/or treating Alzheimer's disease and/or dementia with Lewy bodies, as an effective component for a pharmaceutical composition. Thus, in another aspect, the present disclosure relates to a pharmaceutical composition containing the peptide mimetic of the present disclosure, used in a method for preventing, ameliorating, and/or treating Alzheimer's disease and/or dementia with Lewy bodies.

Alternatively, the peptide mimetic of the present disclosure can be used as a probe of ASPD or an imaging probe or a precursor thereof, and can be used in a method for detecting and/or measuring ASPD, an ASPD imaging method, and a method for determining and/or diagnosing severity of a clinical condition of Alzheimer's disease and/or dementia with Lewy bodies. Thus, in another aspect, the present disclosure relates to a composition, a pharmaceutical composition, or a kit including the peptide mimetic of the present disclosure, for detecting and/or measuring ASPD, for imaging ASPD, or for determining and/or diagnosing severity of a clinical condition of Alzheimer's disease and/or dementia with Lewy bodies.

Further, in another aspect, the present disclosure relates to a method for screening a peptide mimetic or a low molecular weight compound used in a method for inhibiting the interaction between ASPD and NAKα3, suppressing death of mature neurons induced by ASPD, or preventing, ameliorating, and/or treating Alzheimer's disease and/or dementia with Lewy bodies, including performing Structure-Based Drug Design (SBDD) based on a tertiary structure of the first polypeptide. The screening method may include checking ASPD binding ability regarding a candidate compound designed by the SBDD and produced and/or the suppression of death of mature neurons induced by ASPD.

[Polynucleotide and Vector]

In still another aspect, the present disclosure relates to a polynucleotide encoding the polypeptide of the present disclosure, and also relates to a vector including the polynucleotide encoding the polypeptide of the present disclosure, for expressing the polypeptide. Although the vector is not particularly limited as long as it can gene-transfer the polynucleotide, the vector is preferably an adeno-associated virus (AVV) vector from the viewpoint of safety. As a preferred embodiment of the vector of the present disclosure, there is a form in which the vector binds to the brain-migrating peptide. By allowing the vector to bind to the brain-migrating peptide, efficiency at which the vector of the present disclosure migrates to the brain beyond the blood-brain barrier can be enhanced. As the brain-migrating peptide, those which are conventionally known can be used.

[Pharmaceutical Composition]

In the case where the present disclosure is a pharmaceutical composition, a dosage form can be selected appropriately depending upon an administration method, and examples of the dosage form include an injection, a liquid formulation, a capsule, a masticatory, a tablet, a suspension, a cream, and an ointment. The administration method is not particularly limited, either, and examples thereof include oral administration and parenteral administration. The pharmaceutical composition of the present disclosure may contain a conventionally known additive (for example, a vehicle or a diluent) in accordance with an administration form or a dosage form.

Examples of the dosage form suitable for oral administration include solid formulations such as a tablet, particles, liquid, a powder-containing capsule, a troche, a masticatory, multiparticles and nanoparticles, a gel, and a film; and liquid formulations such as a suspension, a solution, a syrup, and an elixir. Examples of the vehicle include supports such as cellulose, calcium carbonate, calcium secondary phosphate, mannitol, and sodium citrate; granulated binders such as polyvinylpyrrolidone, hydroxypropylcellulose, hydroxypropylmethylcellulose, and gelatin; disintegrators such as starch sodium glycolate and a silicate; lubricates such as magnesium stearate and stearic acid; humectants such as sodium lauryl sulfate; a preservative; an antioxidant; correctives; and a colorant.

Examples of parenteral administration of a pharmaceutical composition of the present disclosure include direct administration to a blood flow, a muscle, or an internal organ. The parental administration includes intravenous administration, intraarterial administration, intraperitoneal administration, intrathecal administration, ventricular administration, intraurethral administration, sternal administration, intramedullary administration, intramuscular administration, and subcutaneous administration. The parenteral administration can be performed with a syringe, a needleless syringe, and other injection techniques. Further, an example of the dosage form suitable for the parenteral administration is an aqueous solution containing a vehicle and/or a buffer.

[Method for Prevention, Amelioration, and/or Treatment]

In the present specification, prevention of Alzheimer's disease and/or dementia with Lewy bodies includes suppressing onset of Alzheimer's disease and/or dementia with Lewy bodies, or preventing a clinical condition from progressing further from reversible moderate cognitive impairment. Further, in the present specification, amelioration of Alzheimer's disease and/or dementia with Lewy bodies includes the following state: a clinical condition of reversible moderate cognitive impairment of Alzheimer's disease and/or dementia with Lewy bodies stops progressing or a clinical condition becomes moderate. Further, in the present specification, treatment of Alzheimer's disease and/or dementia with Lewy bodies includes delaying progression of a clinical condition or substantially stopping the progression.

A preferred embodiment of the present aspect includes administering the pharmaceutical composition of the present disclosure containing a polypeptide, a peptide mimetic, or a low molecular weight compound to a subject. It is preferred that the treatment or prevention method of the present aspect include administering an effective amount of the pharmaceutical composition of the present disclosure to a subject. In the case where a subject is a human, for example, a total amount per day of a polypeptide, a peptide mimetic, or a low molecular weight compound can be set generally in a range of 0.0001 mg/kg to 100 mg/kg. Further, a total amount per day can be administered in a single dose or divided doses. As the administration method, the above-mentioned oral/parenteral administration can be selected appropriately.

[Imaging Method]

In another aspect, the present disclosure relates to an ASPD imaging probe or a precursor thereof including the polypeptide or the peptide mimetic of the present disclosure as a binding portion with respect to ASPD. By labeling the polypeptide or the peptide mimetic of the present disclosure with an appropriate labeled radioactive compound, an ASPD imaging probe can be obtained.

Further, in another aspect, the present disclosure relates to an ASPD imaging method. The imaging method can be performed by detecting a signal of the probe for imaging from a subject (preferably, the brain of the subject) administered with the probe after an elapse of a predetermined period of time from administration of the probe. Examples of the subject include humans and animals other than humans (mammals). Further, detection of a signal of the probe includes, for example, detecting a signal of a radioactive nuclide used for labeling the probe for imaging. The imaging method of the present disclosure further may include reconfiguring the detected signal so as to convert it into an image, and further, may include displaying the converted image. Further, in the imaging method of the present disclosure, detection of a signal can be determined appropriately in accordance with a kind of a radioactive nuclide of a molecular probe to be used, and can be performed by, for example, measurement using PET, measurement using SPECT, etc.

The measurement using SPECT includes, for example, measuring a γ-ray released from a subject administered with the probe for imaging with a gamma camera. The measurement with a gamma camera includes, for example, measuring a radiation (γ-ray) emitted from the radioactive nuclide used for labeling the probe for imaging on a predetermined time basis, and preferably includes measuring a direction in which the radiation is released and a radiation quantity on a predetermined time basis. The imaging method of the present disclosure further may include displaying a measured distribution of the probe for imaging of the present disclosure obtained by measuring a radiation as a cross-sectional image and reconfiguring the obtained cross-sectional image.

The measurement using PET includes, for example, simultaneously counting, with a PET detector, a pair of annihilation radiations generated by the binding between a positron and an electron from a subject administered with the probe for imaging, and further may include drawing a three-dimensional distribution of a position of the radioactive nuclide releasing the positron, based on the measured result.

In the imaging method of the present disclosure, X-ray CT or MRI measurement may be performed together with the measurement using SPECT or the measurement using PET. Consequently, for example, a fusion image in which an image obtained by SPECT or an image obtained by PET (functional image) is fused with an image obtained by CT or an image obtained by MRI (morphological image) can be obtained.

[Determination/Diagnosis Method]

An ASPD amount may be calculated based on signal data or image data obtained by the ASPD imaging method of the present disclosure. A native ASPD amount in the cerebral cortex of a patient suffering from Alzheimer's disease and/or dementia with Lewy bodies increases relative to severity of Alzheimer's disease and/or dementia with Lewy bodies, and hence, severity of a clinical condition of Alzheimer's disease and/or dementia with Lewy bodies can be determined or diagnosed by performing the imaging method of the present disclosure. Thus, in another aspect, the present disclosure relates to a diagnosis method including determining severity of a clinical condition of Alzheimer's disease and/or dementia with Lewy bodies, based on the signal data or the image data obtained by the ASPD imaging method.

The number of neurons expressing NAKα3 in the cerebral cortex of a patient suffering from Alzheimer's disease and/or dementia with Lewy bodies decreases relative to severity of Alzheimer's disease and/or dementia with Lewy bodies. Therefore, severity of a clinical condition of Alzheimer's disease and/or dementia with Lewy bodies can be determined or diagnosed also by imaging NAKα3. Thus, in another aspect, the present disclosure relates to a method for diagnosing a clinical condition of Alzheimer's disease and/or dementia with Lewy bodies, including determining severity of a clinical condition of Alzheimer's disease and/or dementia with Lewy bodies based on signal data or image data obtained by an NAKα3 imaging method which includes detecting a signal of an NAKα3 imaging probe including a binding partner of NAKα3 as a binding portion with respect to NAKα3 from a subject administered with the imaging probe, or based on a result of measurement of an NAKα3 amount calculated from the signal data or the image data. An example of the binding partner of NAKα3 is anti-NAKα3 antibodies. Further, imaging of NAKα3 can be performed similarly to imaging of ASPD.

Hereinafter, one or a plurality of embodiments of the present disclosure is further described by way of examples.

EXAMPLES

Figure 3:
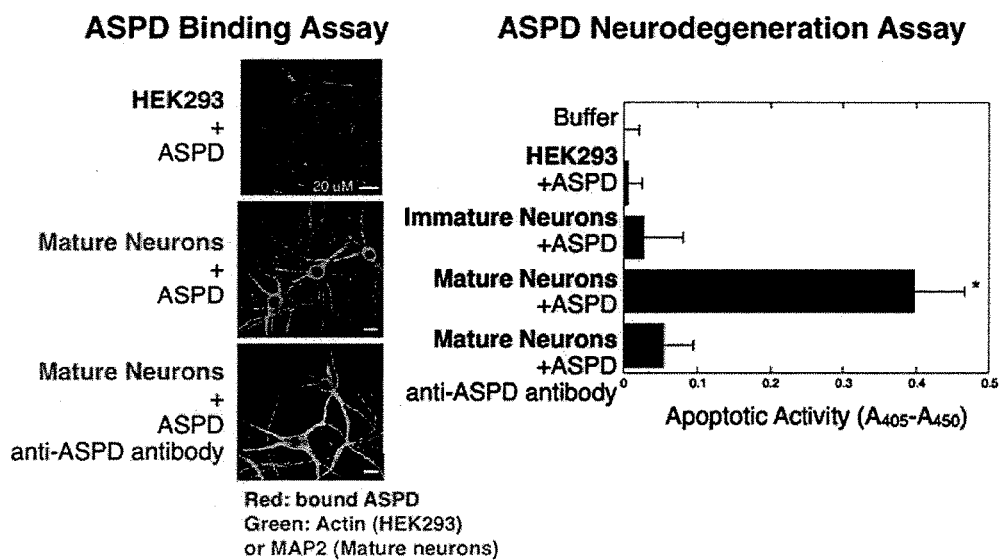
FIG. 3 shows an example of results of an ASPD binding assay (left photograph) and an ASPD toxicity test (right graph).

1. Although ASPD Exhibits Toxicity to Mature Neurons, it does not Exhibit Toxicity to Immature Neurons or HEK293 Cells that are Non-Neuronal Cells (1-1) ASPD Binding Assay After synthetic ASPD was purified with a filter, the synthetic ASPD was administered to human fetus-derived HEK 293 cells and mature rat hippocampus-derived primary cultured neurons, and immobilized and subjected to immunohistostaining one hour later. ASPD bound to the mature neurons without binding to the HEK293 cells. FIG. 3 shows the result on the left side. As shown in FIG. 3, the binding between ASPD and the mature neurons was inhibited by anti-ASPD antibodies.

(1-2) ASPD Toxicity Test

A predetermined concentration of ASPD (5 μM) was administered to the respective cells, and the cells were allowed to stand overnight. After that, apoptotic activity was determined through use of Cell Death ELISA produced by Hoffmann-La Roche Ltd. ASPD exhibited toxicity only to the mature neurons without exhibiting toxicity to the HEK293 cells that were non-neuronal cells and the rat hippocampus-derived primary cultured neurons. FIG. 3 shows the result on the right side. As shown in FIG. 3, the toxicity of ASPD to the mature neurons was inhibited by the anti-ASPD antibodies.

(1-3) The Above-Mentioned Description and FIG. 3 Suggested that ASPD Binds to a Target Molecule Present Only on the Surface of the Mature Neurons and Exhibits Neurotoxicity Due to the Specific Tertiary Structure Thereof.

Figure 4:
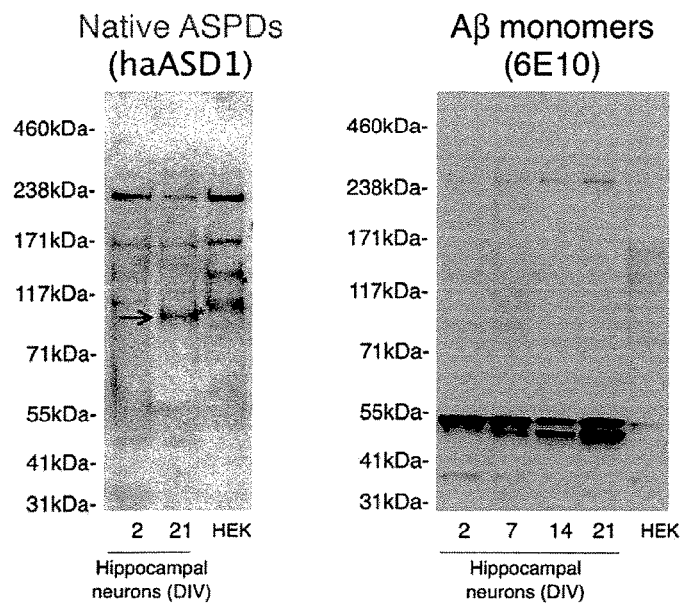
FIG. 4 shows an example in which far-western blotting is performed using anti-ASPD antibodies (haASD1) and anti-Aβ monomer antibodies (6E10).

2. Immobilization of $Na^+/K^+$-ATPase α3 that is a Target Molecule of ASPD (2-1) Analysis by Far-Western Blotting Extracts were prepared with RadioImmunoPrecipitation Assay (RIPA) respectively from the rat hippocampus-derived primary cultured neurons (number of culture days shown in FIG. 4) and the HEK293 cells, and protein amounts of the extracts were determined. Then, predetermined amounts of the extracts were subjected to electrophoresis with SDS-PAGE and transcribed to a nitrocellulose membrane, and reacted with native ASPD or an Aβ monomer for a predetermined period of time. The binding of the native ASPD was detected with anti-ASPD antibodies haASD1, and the binding of the Aβ monomer was detected with 6E10 that was commercially available anti-Aβ monomer antibodies (far-western blotting). FIG. 4 shows the result.

As shown in FIG. 4, it was found that ASPD recognizes a 105 kDA band only in the extract derived from the mature neurons. On the other hand, the Aβ monomer did not bind to the band and recognized a band of about 50 kDa. The binding between the native ASPD and the 105 kDA band was specific to ASPD, and hence, the band was not detected only with the anti-ASPD antibodies in the absence of ASPD. Even in the case where the native ASPD was treated with an excess amount of anti-ASPD antibodies in advance, the band was not detected. This relates to the fact that the binding and toxicity of ASPD to the mature neurons are lost in pre-treatment with the anti-ASPD antibodies.

(2-2) Analysis by Mass Spectrometry

Figure 5:
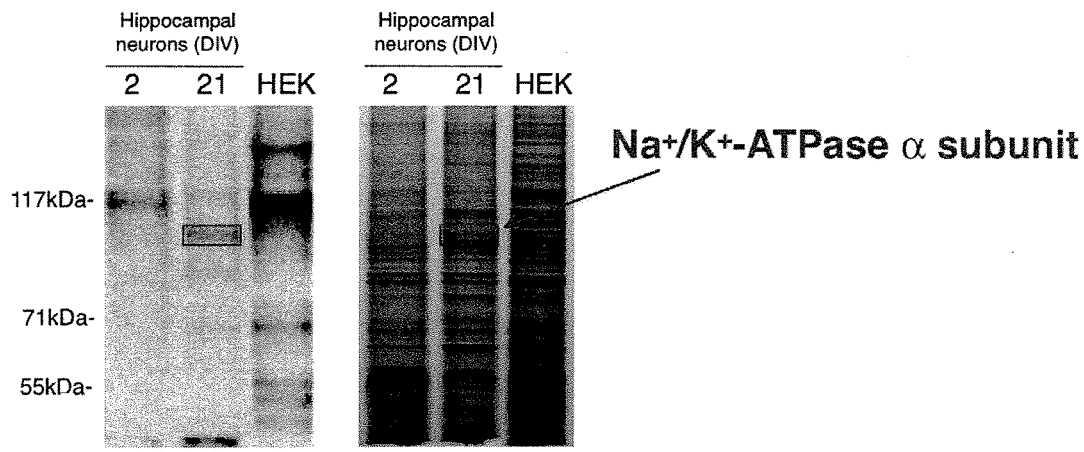
FIG. 5 shows an example of far-western blotting (left) and a silver staining pattern (right).

FIG. 5 shows, on the left side, the result of far-western blotting in the case of using synthetic ASPD instead of the native ASPD of FIG. 4. Similarly to the native ASPD (left side of FIG. 4), it is shown that synthetic ASPD binds to a 105 kDa band only in the mature neurons. Thus, the synthetic ASPD is considered to be equivalent to the native ASPD, and after that, analysis was carried out using the synthetic ASPD.

FIG. 5 shows, on the right side, a silver staining pattern of an extract derived from cells used on the left side of FIG. 5. A band that could not be detected with an extract derived from immature neurons or an extract derived from the HEK293 cells was recognized in a region surrounded rectangularly. This band was cleaved and subjected to tandem mass spectrometry (MS/MS) analysis with a mass spectrometer (MALDI-TOF-MS, produced by Bruker Daltonics K.K., trade name: Ultraflex), and consequently, an $Na^+/K^+$-ATPase a subunit was detected.

(2-3) Confirmation of α3 Subunit

Figure 6:
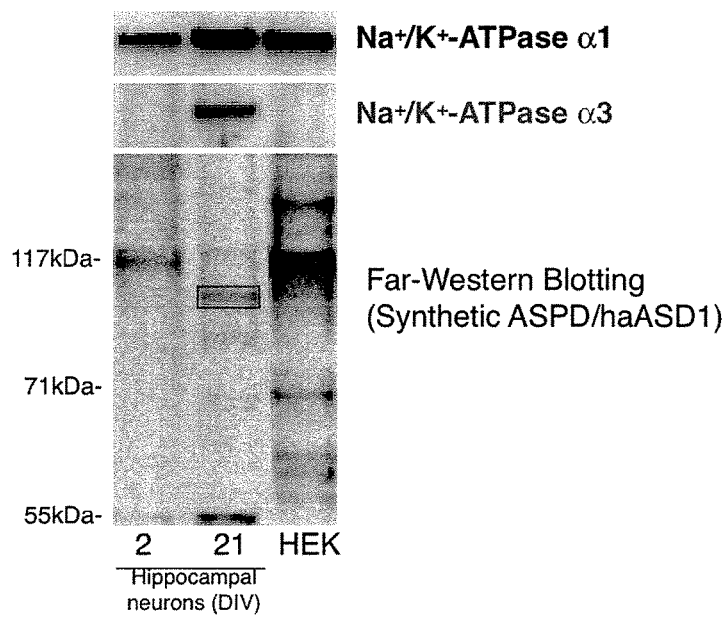
FIG. 6 shows an example of far-western blotting (lower stage), and western blotting using anti-Na$^+$/K$^+$-ATPase α1 (NAKα1) antibodies (upper stage) and anti-Na$^+$/K$^+$-ATPase α3 (NAKα3) antibodies (middle stage).

Western blotting using antibodies selective to the $Na^+/K^+$-ATPase a1 subunit and the α3 subunit was performed through use of the extracts used in far-western blotting on the left side of FIG. 4 and the left side of FIG. 5. FIG. 6 shows the result. As shown in FIG. 6, it was reported that the α3 subunit is expressed selectively in the mature neurons, and a target bound by ASPD is an Na$^+$/K$^+$-ATPase α3 subunit (NAKα3).

(2-4) Coprecipitation of NAKα3 in ASPD Immunoprecipitation

Figure 7:
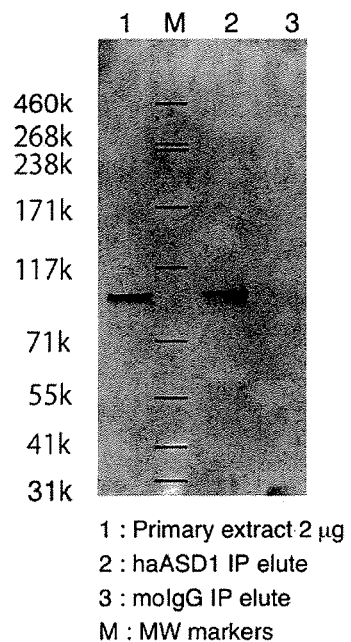
FIG. 7 shows an example in which an immunoprecipitate obtained with anti-ASPD antibodies (haASD1) is subjected to western blotting with anti-NAKα3 antibodies.

An extract of the mature rat hippocampus-derived primary cultured neurons, an immune precipitate obtained by adding synthetic ASPD to the extract and using anti-ASPD antibodies (haASD1), and an immune precipitate obtained by adding synthetic ASPD to the extract and using normal mouse IgG as a control were subjected to electrophoresis, whereby western blotting was performed with NAKα3 specific antibodies. FIG. 7 shows the result. As shown in FIG. 7, it was clarified that NAKα3 is coprecipitated with ASPD due to the presence of the anti-ASPD antibodies.

(2-5) Coprecipitation of NAKα3 in ASPD Immunoprecipitation

Figure 8:
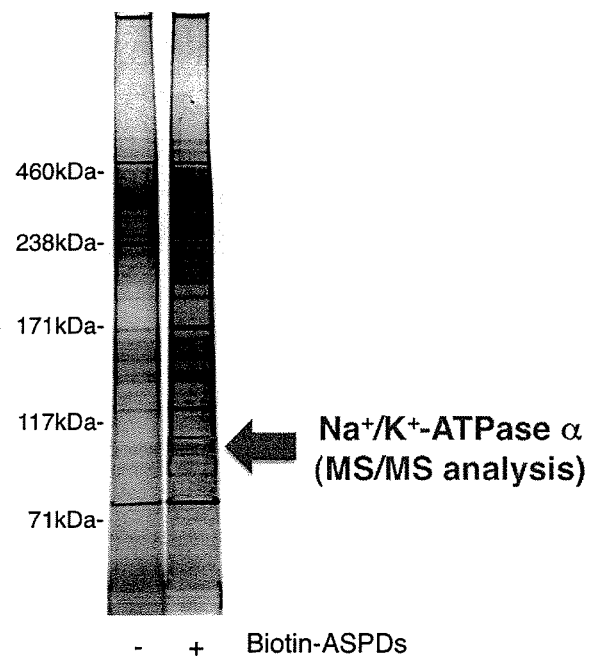
FIG. 8 shows an example of a silver staining pattern of an avidin fraction obtained from mature neurons administered with biotinylated ASPD.

The above-mentioned experiment (2-4) showed that ASPD and NAKα3 interact with each other directly. In order to verify that the interaction occurs on living cells, biotinylated ASPD in which biotinylated Aβ was mixed in a predetermined ratio was prepared and administered to living mature neurons (rat hippocampus-derived primary cultured neurons), a cell membrane was collected under the condition of not breaking ASPD structure within one hour from the administration, and the cell membrane was fractioned with avidin having strong affinity to biotin. FIG. 8 shows the result of a silver staining. As shown in FIG. 8, there is a band recognized at around 105 kDa only under the condition of the biotinylated ASPD administration, and it was clarified from tandem mass spectrometry (MS/MS) analysis that the band is NAKα. The above-mentioned two different experiments (2-4) and (2-5) showed that ASPD and NAKα3 interact with each other directly with sufficient binding strength.

(2-6) Fluorescent Microscope Observation

Figure 9:
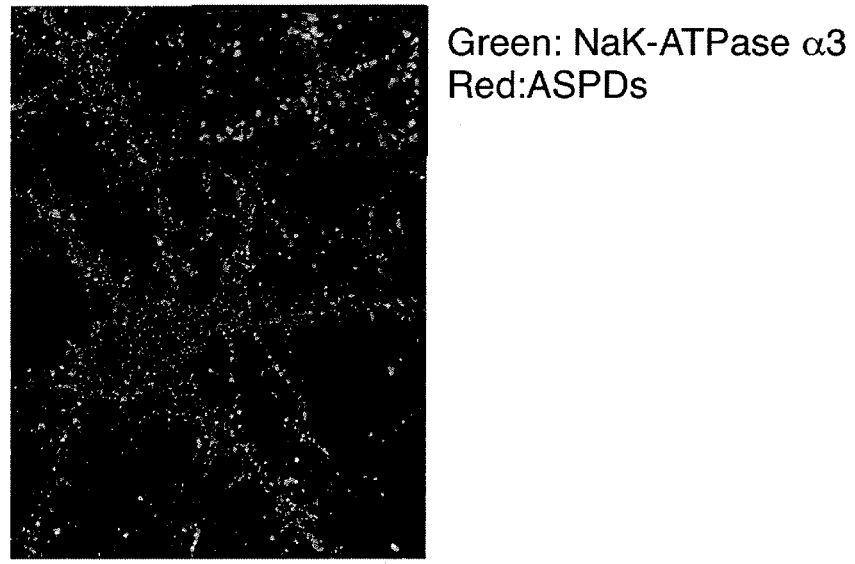
FIG. 9 shows an example of a photograph of ASPD binding site detected by anti-ASPD antibodies (red) and NAKα3 localization (green) in mature neurons detected by NAKα3 antibodies observed with a fluorescence microscope.

FIG. 9 shows the result obtained by administering synthetic ASPD to mature neurons (rat hippocampus-derived primary cultured neurons), subjecting a binding site of ASPD on the mature neurons to fluorescent staining with anti-ASPD antibodies, subjecting an existing site of NAKα3 to fluorescent staining with specific antibodies, and observing the existing site with a fluorescent microscope. As shown in FIG. 9, a site to which ASPD binds is matched with the existing site of NAKα3.

(2-7) Dissociation Constant

Figure 10:
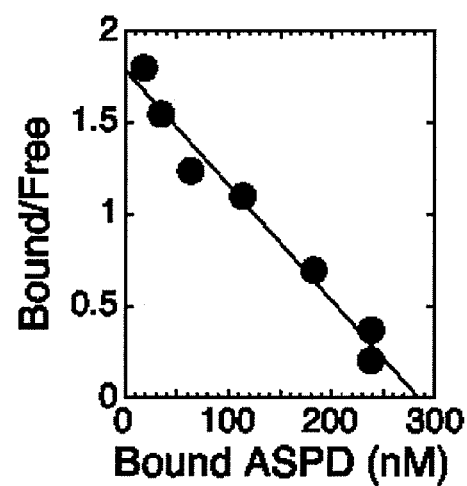
FIG. 10 shows an example of a Scatchard plot of a result obtained by administering synthetic ASPD to mature neurons, immobilizing the cells one hour later, and determining the amount of ASPD that binds to the cells through use of anti-ASPD antibodies.

FIG. 10 shows an example of a Scatchard plot of a result obtained by administering synthetic ASPD to mature rat hippocampus-derived primary cultured neurons, immobilizing the cells one hour later, and determining quantity of ASPD that binds to the cells through use of anti-ASPD antibodies. Further, it is shown from the Scatchard plot of FIG. 10 that a dissociation constant of the synthetic ASPD is Kd=1.5±7.8×10$^{-7}$ M.

(2-8) Inhibition of ATPase Activity of NAKα3 by ASPD

Figure 11:
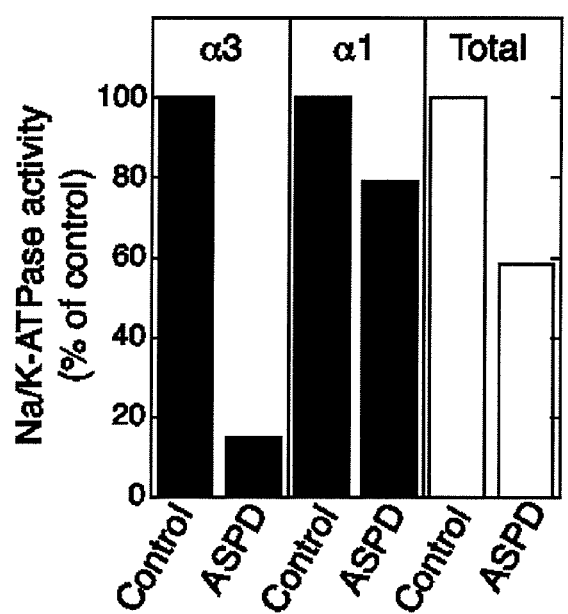
FIG. 11 shows an example of a result obtained by measuring activity inhibition of NAKα3 and NAKα1 by ASPD.

Synthetic ASPD was administered to mature rat hippocampus-derived primary cultured neurons, and a cell membrane was collected about 24 hours later. Then, ATPase activity was measured, and NAK activity was obtained through use of ouabain that was a selective inhibitor of NAK. In the rat, Ki of the ouabain is α3=3.1±0.3×10$^{-8}$ M, α1=4.3±1.9×10$^{-5}$ M. In the presence of a low concentration of ouabain (10 nM), only NAKα3 is inhibited, and hence, NAKα3 activity can be obtained (graph in a left column of FIG. 11). As activity not inhibited in the presence of 10 nM of ouabain but inhibited by 100 μM of ouabain, NAKα1 activity (graph in a middle column of FIG. 11) can be obtained. As shown in FIG. 11, it was found that the NAKα3 activity reached 20% or less due to the ASPD treatment. On the other hand, it was clarified that the NAKα1 activity did not decrease, compared with the NAKα3 activity. Thus, it was clarified that ASPD strongly inhibits, in particular, the NAKα3 activity.

(2-9) Regarding NAKα3

Figure 12:
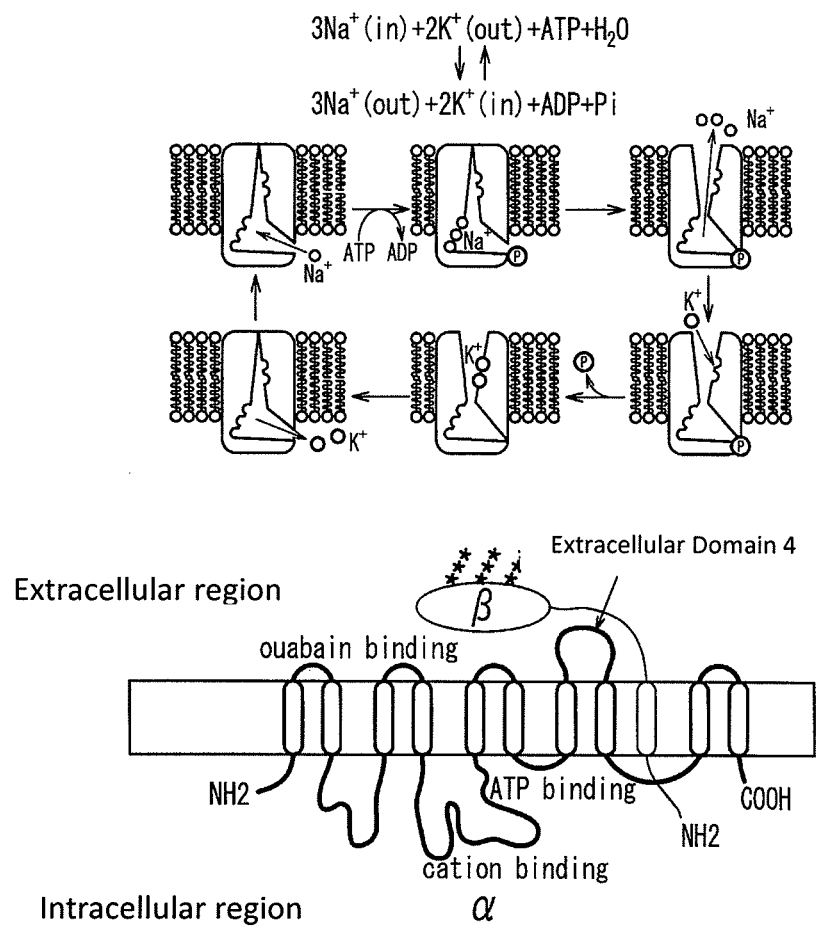
FIG. 12 shows a function, a structure, and an expression distribution of NAKα3.

FIG. 12 shows a function, a structure, and a distribution of Na$^+$/K$^+$-ATPase (NAK). An upper figure of FIG. 12 is an exemplary explanatory view of a sodium-potassium pump function conjugated with ATP hydrolysis, which is a NAK function. A middle figure of FIG. 12 shows an example of structures of an α subunit and a β subunit of NAK. As shown in this figure, it has been reported that the β subunit binds to the extracellular domain 4 of the α subunit (Lemas et al., vol. 269, 8255-8259, 1994). As shown in a table of a lower figure of FIG. 12, the α1 subunit is a ubiquitous type present in all the cells. On the other hand, an α3 subunit is expressed selectively in mature neurons. It is known that, although an α2 subunit is expressed in immature neurons, the α2 subunit is switched to the α3 subunit when the immature neurons mature. The findings of NAKα3 are well matched with the results of FIGS. 3 to 11.

Figure 13:
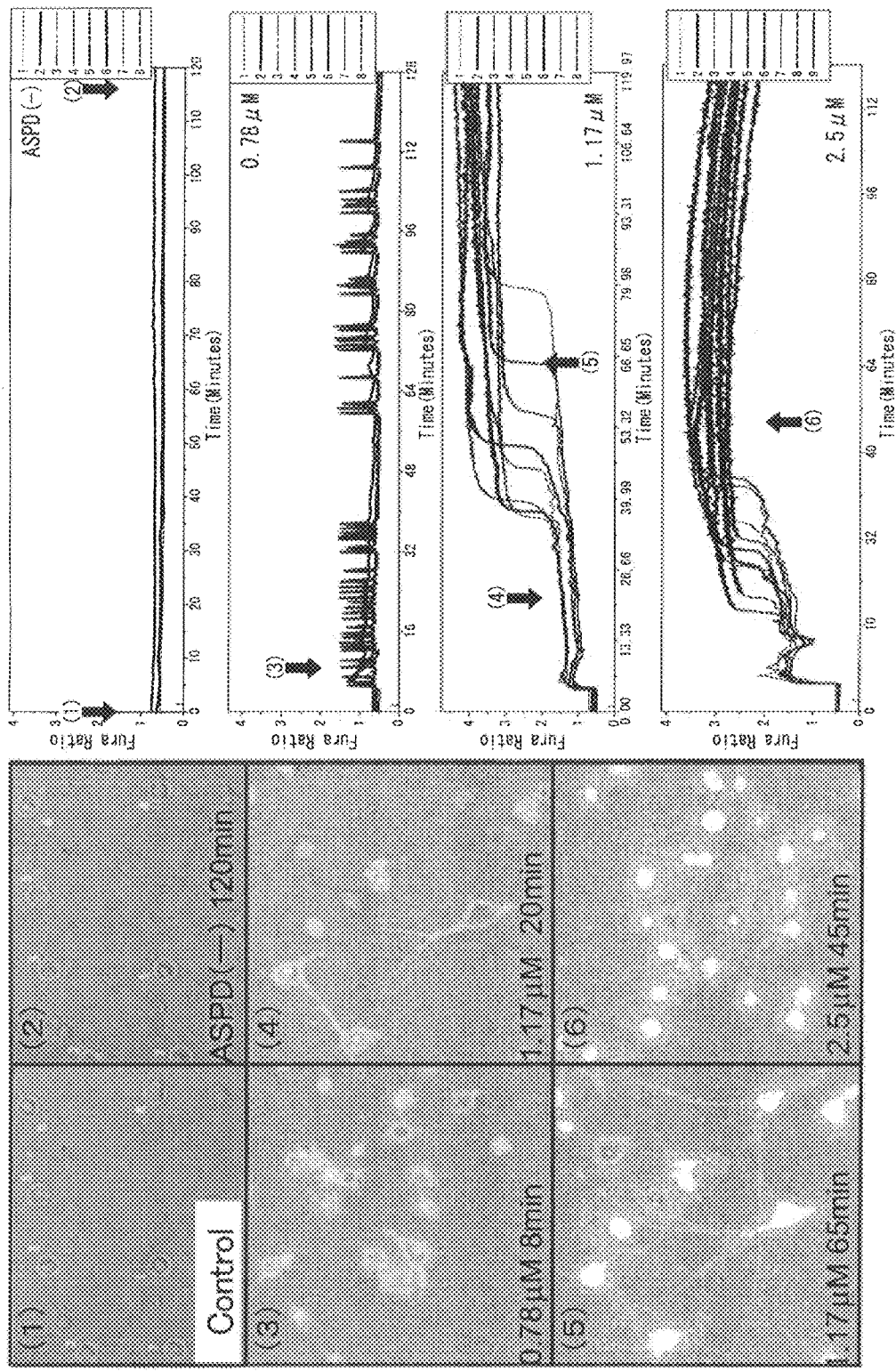
FIG. 13 shows an example of a result obtained by measuring a calcium concentration in mature neurons triggered by the treatment with ASPD.

3. Mechanism for Death of Cells Triggered by ASPD (3-1) Measurement of Intracellular Calcium Concentration Assuming that the activity of NAKα3 is inhibited when ASPD binds to NAKα3, the following was predicted: (1) flowed Na is not drawn, and hence, a membrane potential increases; consequently, a Ca channel dependent upon a membrane potential is opened, or (2) an Na/Ca exchanger (NCX) on a cell membrane reacts to take in Ca in response to the increase in Na, and an extraordinary flow of calcium occurs in cells finally. Then, an intracellular calcium concentration when ASPD was administered to mature rat hippocampus-derived primary cultured neurons was observed with a fluorescent calcium indicator, Fura PE3. FIG. 13 shows the result. As shown in FIG. 13, it was found that an increase in the intracellular calcium concentration was detected immediately after the administration of ASPD, and the intracellular calcium concentration finally reached to the maximum limit, thereby causing death of cells. It also was shown that this occurs faster depending upon the concentration of ASPD.

(3-2) Effect of Calcium Channel Inhibitor

Figure 14:
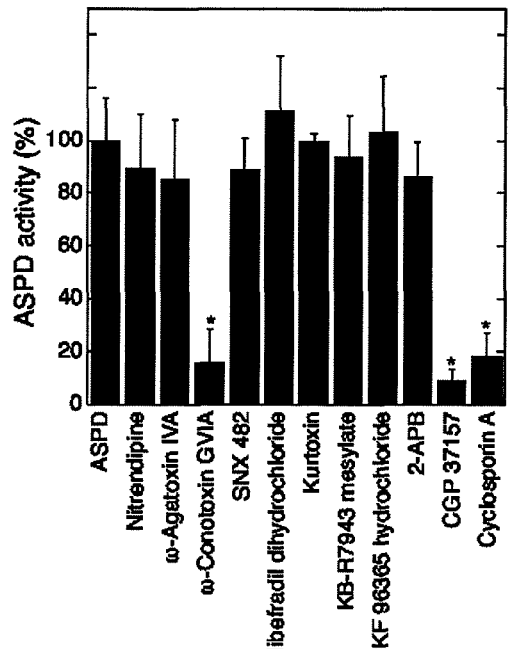
FIG. 14 shows an example of a result obtained by elucidating the effect of various calcium channel inhibitors on ASPD activity (apoptotic activity).
Figure 15:
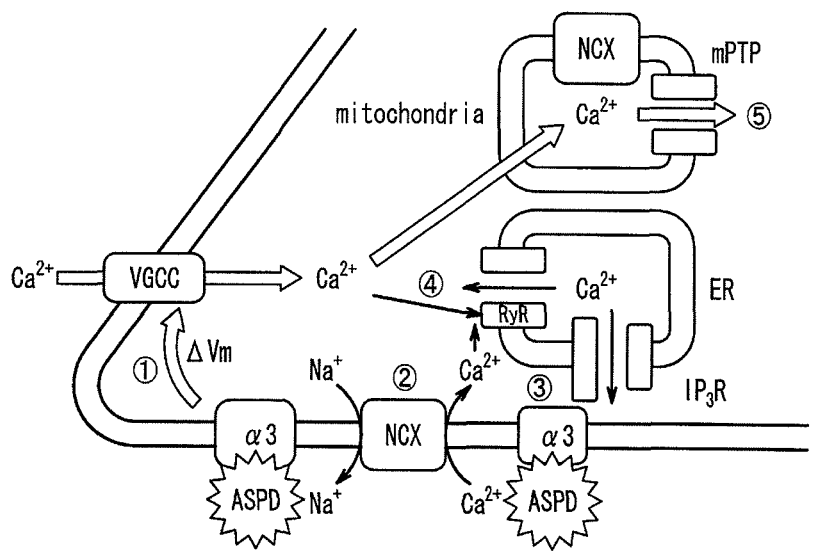
FIG. 15 is an explanatory diagram of a mechanism of death of neurons.

Various kinds of inhibitors shown in the following Table 1 were administered in advance to mature rat hippocampus-derived primary cultured neurons in concentrations shown in Table 1, 4 μM of synthetic ASPD was administered to the mature rat hippocampus-derived primary cultured neurons 30 minutes later, and apoptotic activity was measured 24 hours later. Table 1 and FIG. 14 show the result. As shown in Table 1 and FIG. 14, it was found that, among membrane potential dependent calcium channels, N-type channels, present in a large number in the presynapse, relate to a neuron death signal cascade occurring due to the suppression of NAKα3 activity after the administration of ASPD. Further, it also was found that NCX and mPTP present in mitochondria also contribute to the neuron death signal cascade. Thus, as shown in FIG. 15, it was clarified that a flow of calcium into cells first occurs when membrane potential-dependent N-type calcium channels on the synapse are activated, and calcium metabolic disorder of mitochondria occurs, which leads to death of cells.

TABLE 1

| Calcium channel | Inhibitor | Concentration (μM) | Effect of inhibition |
|---|---|---|---|
| Ca$^{2+}$ channel blocker (L-type) | Nitrendipine | 1.0 | – |
| Ca$^{2+}$ channel blocker (P-type) | ω-Agatoxin IVA | 2.5 | – |
| Ca$^{2+}$ channel blocker (N-type) | ω-Conotoxin GVIA | 4.0 | + |
| Potent and selective CaV2.3 blocker (R-type) | SNX482 | 1.0 | – |
| Ca$^{2+}$ channel blocker (T-type) | Mibefradil dihydrochloride | 1.0 | – |
| Ca$^{2+}$ channel blocker (T-type) | Kurtoxin | 1.0 | – |
| Na$^+$/Ca$^{2+}$ exchange inhibitor | KB-R7943 mesylate | 30.0 | – |
| STIM1-mediated Ca$^{2+}$ influx inhibitor | SKF96365 | 30.0 | – |
| IP3 receptor antagonist | 2-APB | 10.0 | – |
| Antagonist of mitochondrial Na$^+$/Ca$^{2+}$ exchange | CGP 37157 | 3.0 | + |
| mPTPopening inhibitor | Cyclosporin A | 20.0 | + |

4. Correlation Between Clinical Condition of Alzheimer's Disease and Na$^+$/K$^+$-ATPase α3

Figure 16:
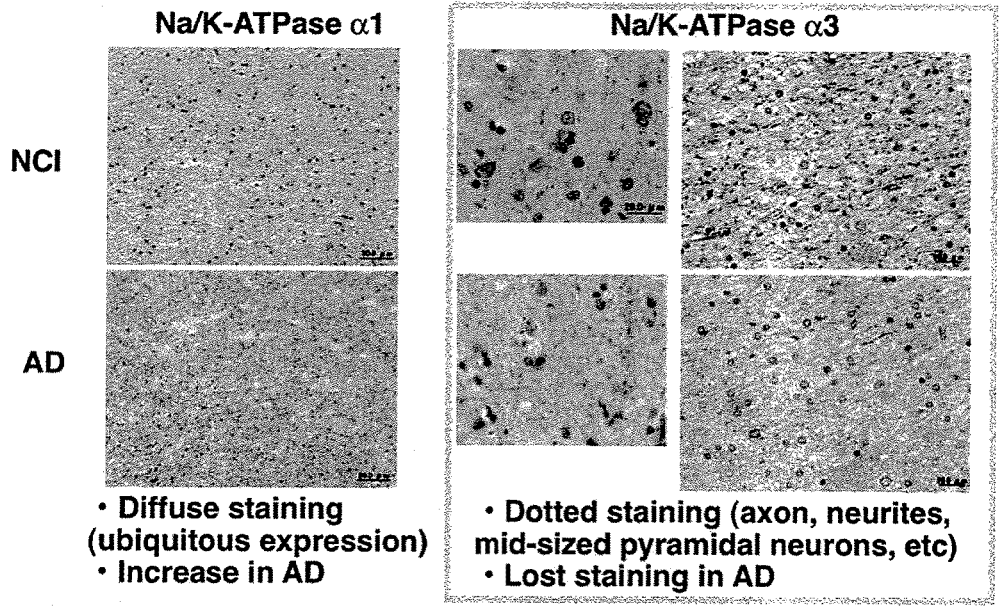
FIG. 16 shows an example of a result obtained by subjecting NAKα3 and NAKα1 in the cerebral cortex of normal (age-matched non-demented people) and Alzheimer's disease (AD) patients to histological staining with antibodies.
Figure 17:
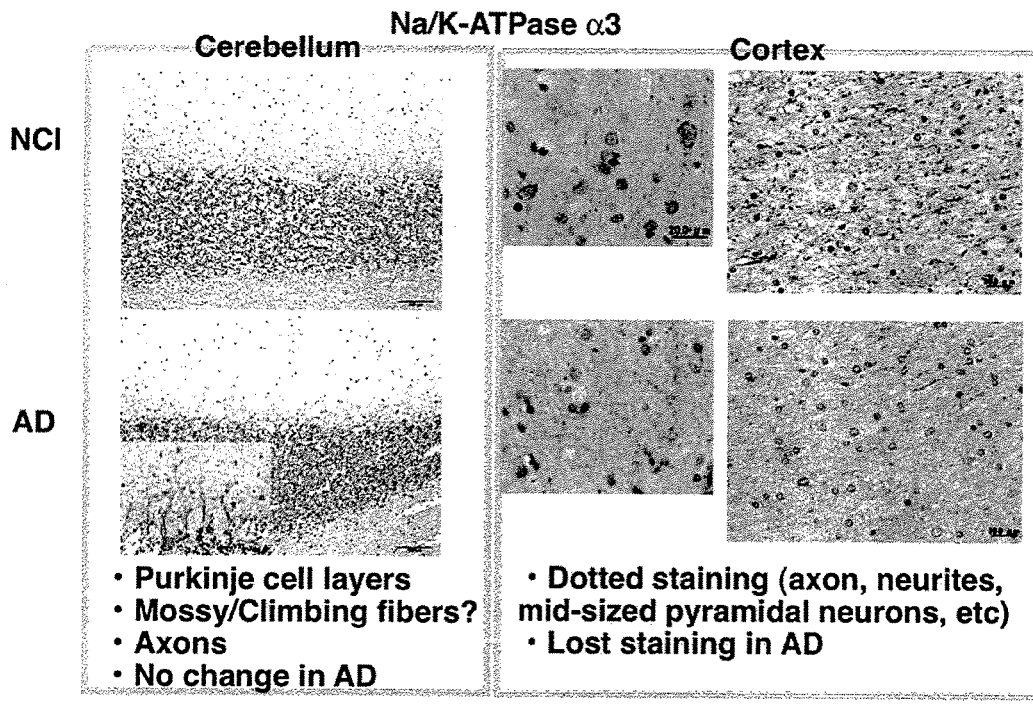
FIG. 17 shows an example of a result obtained by subjecting NAKα3 in the cerebellum of normal (age-matched non-demented people) and AD patients to histological staining with antibodies.

A distribution of NAK was verified in the human brain through use of specific antibodies. According to the analysis in the normal brain, first, NAKα1 was distributed entirely, which was matched with the fact that NAKα1 is present ubiquitously (upper left of FIG. 16). On the other hand, it was found that NAKα3 exhibits a distribution completely different from that of NAKα1, and in the cerebral cortex, NAKα3 is distributed so as to be in a dot shape along neurites or axons or so as to surround pyramidal cells (neurons) (upper right of FIG. 16). In the cerebellum, NAKα3 was present in a dot shape along the neurites or axons and distributed so as to surround Purkinje cells (upper left of FIG. 17). This overlaps the distribution of Basket cells very well. The Basket cells are present also in the cerebral cortex, which is matched with the fact that NAKα3 is often recognized to be expressed in inhibitory nerves in the expression analysis of mRNA. In the patient brain, staining of NAKα3 was lost in the cerebral cortex in which disorders were largely recognized in Alzheimer's disease (lower right of FIG. 16). On the other hand, the following result was obtained: although staining of NAKα1 was lost in an original existing site, an amount of staining rather increased in other portions (lower left of FIG. 16). This is the result matched with the analysis of mRNA in the past (Siegel 1998). Simultaneously, an ASPD amount was examined. As a result, only a very small amount of ASPD at the same level as that of a normal condition was detected in the patient cerebellum, whereas a large amount of ASPD was present in the cerebral cortex in which disorders were serious, which was correlated with a decrease in NAKα3 (Table 2).

TABLE 2

| | ASPD (nmol/ml) n > 3 | NAKα3 | Neuronal loss |
|---|---|---|---|
| NCI cerebral cortex | 0.02 ± 0.01 | ++ | ± |
| AD cerebral cortex | 1.58 ± 0.3 | ± | + |
| AD cerebellum | 0.02 ± 0.02 | ++ | ± |

5. Polypeptide that Binds to ASPD and Suppresses Death of Cells

Based on the fact that anti-ASPD antibodies bind to ASPD to inhibit interaction between ASPD and NAKα3 that is a target molecule to suppress death of neurons, a peptide having similar effect was searched. For this purpose, ASPD immobilized to a microtiter plate was screened through use of (commercially available) phage display library in which a library of random 12 amino acids was expressed on a virus surface, and a converged sequence was analyzed. Phage having the same sequence was obtained a plurality of times repeatedly from a 3rd phage display, which suggests the possibility that some biological concentration occurs and a peptide having binding activity to ASPD is obtained. Further, when all the obtained sequences were analyzed in a bioinformatics manner, H (His) and W (Trp) were expressed significantly at a high frequency. This suggests that peptide motifs that bind to ASPD specifically are included in peptide motifs containing a large amount of H/W. In the peptide motifs, those which actually neutralize ASPD toxicity and those which actually do not neutralize ASPD toxicity were examined. Then, it was found that those which neutralize toxicity have a common motif. A peptide having neutralization activity was named as an Anti-AD toxicity (AAT) peptide. Table 3 shows obtained AAT peptides 01 to 05. Table 3 also shows two examples of peptides (PD) having no neutralization activity.

TABLE 3

| (Table 3) Sequence name | Amino acid sequence | Neutralization activity | SEQ ID |
|---|---|---|---|
| AAT01 | HFNWYNLWRVQY | + | 35 |
| AAT02 | HLNWWHSWYPAR | + | 36 |
| AAT03 | HLNWLSWFPSRH | + | 37 |
| AAT04 | HFNWD | + | 38 |
| AAT05 | HFNWDW | + | 39 |
| PD01 | HHLWRPFWWAEA | – | 40 |
| PD02 | HSWWSSWLRPGT | – | 41 |

Figure 18:
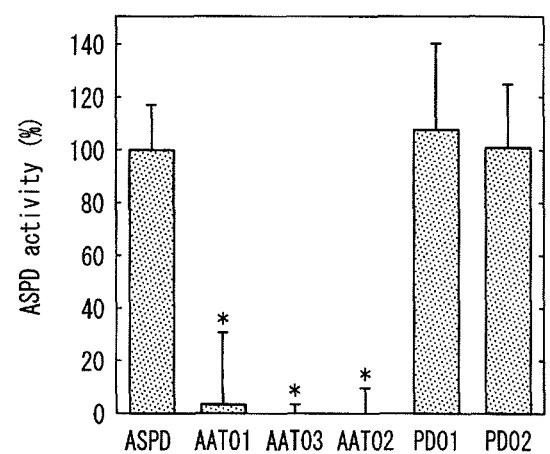
FIG. 18 shows an example of a graph showing inhibition effect of an anti-AD toxicity (AAT) peptide on ASPD activity (apoptotic activity).

To mature rat hippocampus-derived primary cultured neurons, 14 μM of AAT peptide (01 to 03) were administered, 4 μM of synthetic ASPD was administered to the mature rat hippocampus-derived primary cultured neurons 30 minutes later, and apoptotic activity was measured 24 hours later. FIG. 18 shows the result.

Interestingly, regarding the AAT peptide (01 to 03), the first four amino acids (HLNW) are similar to a particular portion (RLNW; greatly different between NAKα3 and NAKα1) of the extracellular domain 4 of NAKα3 that is a target molecule, and the subsequent four amino acids are similar to a portion (Y-NLWR; common between NAKα3 and NAKα1) on a slightly downstream side of the particular portion (FIG. 2). Further, it was suggested that the last four amino acids have no particular motif. Of the motifs of the first four amino acids, the third N (Asn) is specific to NAKα3 (stored in the human and the rat, see FIG. 2), and this was shown to be important.

Figure 19:
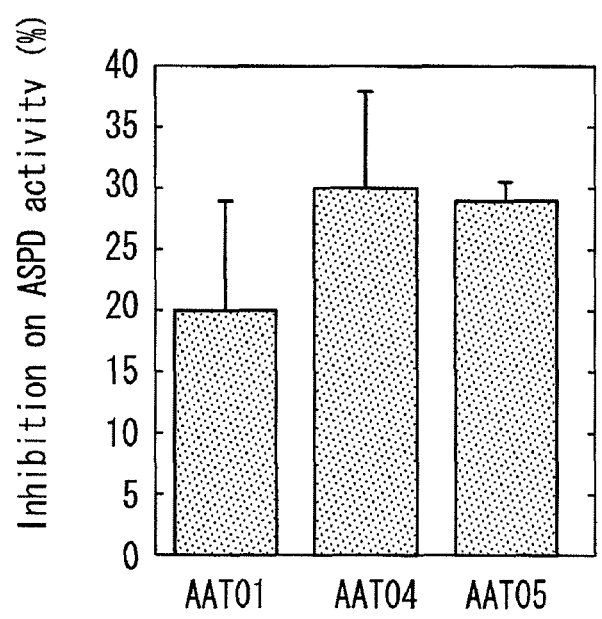
FIG. 19 shows an example of a graph showing inhibition effect of an AAT peptide on ASPD activity (apoptotic activity).

To the mature rat hippocampus-derived primary cultured neurons, 0.14 μM of an AAT peptide (04 to 05) were administered, 4 μM of synthetic ASPD was administered to the mature rat hippocampus-derived primary cultured neurons 30 minutes later, and apoptotic activity was measured 24 hours later. FIG. 19 shows the result. It was clarified that AAT04 and AAT05 obtained by shortening AAT01 have inhibition effect equal to or more than that of the AAT01.

Further, the inhibition effect of apoptotic activity of ASPD was similarly checked through use of AAT peptides 06 and 07 shown in the following Table 4.

TABLE 4

| Sequence name | Amino acid sequence | Neutralization activity | SEQ ID |
|---|---|---|---|
| AAT04 | HFNWD | + | 38 |
| AAT06 | HFNW | + | 42 |
| AAT07 | FNWD | + | 47 |

Figure 20:
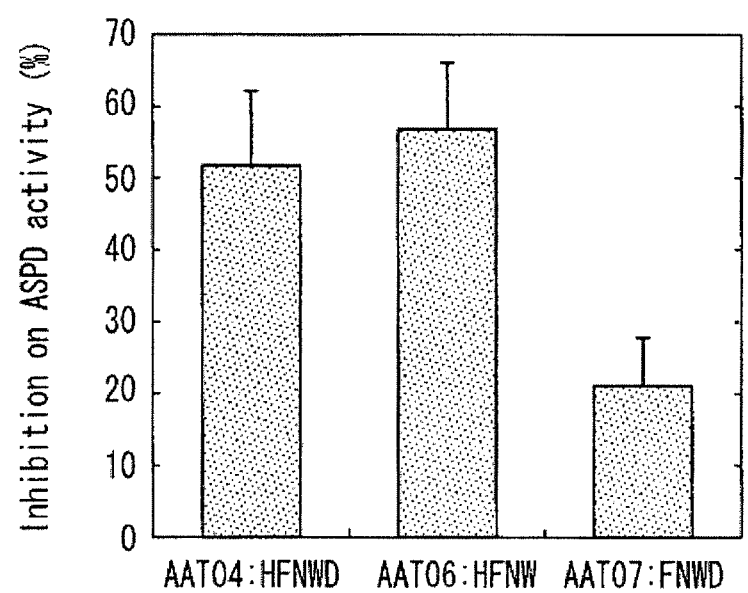
FIG. 20 shows an example of a graph showing inhibition effect of an ATT peptide on ASPD activity (apoptotic activity).

To mature rat hippocampus-derived primary cultured neurons, 2.8 µM of an AAT peptide (04, 06, 07) was administered, and 30 minutes later, 4 µM of synthetic ASPD was administered. The apoptotic activity was measured 24 hours later and compared with that of a control to which the AAT peptide has not been administered, whereby the inhibition activity was calculated. FIG. 20 shows the results. Of the peptides obtained by shortening the AAT04, it was clarified that the AAT06 has inhibition effect equal to or higher than that of the AAT04.

5. Dissociation Constant of ASPD and AAT Peptide

Biotin was bound to each C-terminal side of the above-mentioned AAT peptides 01 to 0.3 and made into a solid phase on a chip, and a dissociation constant was obtained by surface plasmon resonance (SPR) using ASPD as a ligand. Table 5 shows the results.

TABLE 5

| Biotinylated AAT peptide | ka | kd | KD |
|---|---|---|---|
| C-terminal biotinylated AAT01 HFNWYNLWRVQY | $7.64 \times 10^3$ | $4.41 \times 10^{-4}$ | $5.77 \times 10^{-8}$ |
| C-terminal biotinylated AAT02 HLNWWHSWYPAR | $5.60 \times 10^3$ | $4.62 \times 10^{-4}$ | $8.24 \times 10^{-8}$ |
| C-terminal biotinylated AAT03 HLNWLSWFPSRH | $4.96 \times 10^3$ | $4.39 \times 10^{-4}$ | $8.85 \times 10^{-8}$ |

[Sequence Table Free Text]

SEQ ID NO: 7 to 39, 42 to 52: ASPD interacting motif/peptide

SEQ ID NO: 40, 41: ASPD interacting motif/peptide (control)

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for inhibiting protein-protein interaction between amylospheroid and Na+/K+-ATPase α3, consisting of causing at least one substance selected from a group consisting of a polypeptide, a peptide mimetic thereof, and anti-NAKα3 antibody to interact with ASPD or NAKα3, wherein length of the polypeptide is 50 or less amino acids, and wherein the polypeptide comprises the amino acid sequence of $X_1X_2NW$ (SEQ ID NO:8) or $X_2NW$ (SEQ ID NO:49) at the N-terminal, wherein $X_1$ is arginine, histidine, or lysine, and $X_2$ is hydrophobic amino acid residue or glycine.

2. A method according to claim 1, wherein the substance mimics a tertiary structure of a site of ASPD or NAKα3 participating in the protein-protein interaction between ASPD and NAKα3.

3. A method for suppressing death of a mature neuron induced by amylospheroid, comprising inhibiting protein-protein interaction between the amylospheroid and Na+/K+-ATPase α3 by administering to a subject in need thereof at least one substance selected from a group consisting of a polypeptide, a peptide mimetic thereof, and anti-NAKα3 antibody, wherein length of the polypeptide is 50 or less amino acids, and wherein the polypeptide comprises the amino acid sequence of $X_1X_2NW$ (SEQ ID NO:8) or $X_2NW$ (SEQ ID NO:49) at the N-terminal, wherein $X_1$ is arginine, histidine, or lysine, and $X_2$ is hydrophobic amino acid residue or glycine.

4. A method according to claim 3, wherein the protein-protein interaction between the amylospheroid and Na+/K+-ATPase α3 is inhibited by contact between the amylospheroid and the substance capable of performing competitive inhibition based on a surface tertiary structure of both or one of the amylospheroid and the Na+/K+-ATPase α3.

5. A method according to claim 3, wherein the protein-protein interaction between the amylospheroid and Na+/K+-ATPase α3 is inhibited by contact between the amylospheroid and the substance capable of binding to the amylospheroid by competition with the Na+/K+-ATPase α3.

6. A method for preventing, ameliorating, and/or treating Alzheimer's disease and/or dementia with Lewy bodies, comprising suppressing death of a mature neuron induced by amylospheroid by inhibiting protein-protein interaction between the amylospheroid and Na+/K+-ATPase α3 by administering to a subject in need thereof at least one substance selected from a group consisting of a polypeptide, a peptide mimetic thereof, and anti-NAKα3 antibody, wherein length of the polypeptide is 50 or less amino acids, and wherein the polypeptide comprises the amino acid sequence of $X_1X_2NW$ (SEQ ID NO: 8) or $X_2NW$ (SEQ ID NO: 49) at the N-terminal, wherein $X_1$ is arginine, histidine, or lysine, and $X_2$ is hydrophobic amino acid residue or glycine.

7. A method according to claim 6, wherein the protein-protein interaction between the amylospheroid and Na+/K+-ATPase α3 is inhibited by contact between the amylospheroid and the substance capable of performing competitive inhibition based on a surface tertiary structure of both or one of the amylospheroid and the Na+/K+-ATPase α3.

8. A method according to claim 6, wherein the protein-protein interaction between the amylospheroid and Na+/K+-ATPase α3 is inhibited by contact between the amylospheroid and the substance capable of binding to the amylospheroid by competition with the Na+/K+-ATPase α3.

* * * * *

SEQUENCE LISTING

```
<160> NUMBER OF SEQ ID NOS: 47

<210> SEQ ID NO 1
<211> LENGTH: 4
<212> TYPE: PRT
<213> ORGANISM: Homo sapiens

<400> SEQUENCE: 1

Arg Leu Asn Trp
1

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 52
<212> TYPE: PRT
<213> ORGANISM: Homo sapiens

<400> SEQUENCE: 3

Phe Ser Tyr Phe Val Ile Leu Ala Glu Asn Gly Phe Leu Pro Gly Asn
1               5                   10                  15

Leu Val Gly Ile Arg Leu Asn Trp Asp Asp Arg Thr Val Asn Asp Leu
            20                  25                  30
```

```
Glu Asp Ser Tyr Gly Gln Gln Trp Thr Tyr Glu Gln Lys Val Val
        35                  40                  45

Glu Phe Thr Cys
    50
```

<210> SEQ ID NO 4
<211> LENGTH: 52
<212> TYPE: PRT
<213> ORGANISM: Homo sapiens

<400> SEQUENCE: 4

```
Phe Thr Tyr Phe Val Ile Leu Ala Glu Asn Gly Phe Leu Pro Ile His
1               5                   10                  15

Leu Leu Gly Leu Arg Val Asp Trp Asp Arg Trp Ile Asn Asp Val
            20                  25                  30

Glu Asp Ser Tyr Gly Gln Gln Trp Thr Tyr Glu Gln Arg Lys Ile Val
        35                  40                  45

Glu Phe Thr Cys
    50
```

<210> SEQ ID NO 5
<211> LENGTH: 52
<212> TYPE: PRT
<213> ORGANISM: Homo sapiens

<400> SEQUENCE: 5

```
Phe Thr Tyr Phe Val Ile Leu Ala Glu Asn Gly Phe Leu Pro Ser Arg
1               5                   10                  15

Leu Leu Gly Ile Arg Leu Asp Trp Asp Asp Arg Thr Met Asn Asp Leu
            20                  25                  30

Glu Asp Ser Tyr Gly Gln Glu Trp Thr Tyr Glu Gln Arg Lys Val Val
        35                  40                  45

Glu Phe Thr Cys
    50
```

<210> SEQ ID NO 6
<211> LENGTH: 52
<212> TYPE: PRT
<213> ORGANISM: Homo sapiens

<400> SEQUENCE: 6

```
Phe Thr Tyr Phe Val Ile Leu Ala Glu Asn Gly Phe Arg Pro Val Asp
1               5                   10                  15

Leu Leu Gly Ile Arg Leu His Trp Glu Asp Lys Tyr Leu Asn Asp Leu
            20                  25                  30

Glu Asp Ser Tyr Gly Gln Gln Trp Thr Tyr Glu Gln Arg Lys Val Val
        35                  40                  45

Glu Phe Thr Cys
    50
```

<210> SEQ ID NO 7
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Arg, His, or Lys

```
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (3)..(3)
<223> OTHER INFORMATION: Xaa=Asn, Gln, Ser, Thr, Cys, His, Tyr, Trp,
      Phe, or Tyr
<220> FEATURE:
<221> NAME/KEY: MISC_FEATURE
<222> LOCATION: (4)..(4)
<223> OTHER INFORMATION: Xaa=Trp, Phe, or Tyr

<400> SEQUENCE: 7

Xaa Xaa Xaa Xaa
1

<210> SEQ ID NO 8
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Arg, His, or Lys
<220> FEATURE:
<221> NAME/KEY: MISC_FEATURE
<222> LOCATION: (2)..(2)
<223> OTHER INFORMATION: Xaa=hydrophobic amino acid or Gly

<400> SEQUENCE: 8

Xaa Xaa Asn Trp
1

<210> SEQ ID NO 9
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=hydrophobic amino acid or Gly

<400> SEQUENCE: 9

His Xaa Asn Trp
1

<210> SEQ ID NO 10
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 10

His Xaa Asn Trp
1

<210> SEQ ID NO 11
<211> LENGTH: 5
<212> TYPE: PRT
<213> ORGANISM: Artificial Sequence
```

```
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Arg, His, or Lys
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (3)..(3)
<223> OTHER INFORMATION: Xaa=Asn, Gln, Ser, Thr, Cys, His, Tyr, Trp,
      Phe, or Tyr
<220> FEATURE:
<221> NAME/KEY: MISC_FEATURE
<222> LOCATION: (4)..(4)
<223> OTHER INFORMATION: Xaa=Trp, Phe, or Tyr
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid

<400> SEQUENCE: 11

Xaa Xaa Xaa Xaa Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Arg, His, or Lys
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid

<400> SEQUENCE: 12

Xaa Xaa Asn Trp Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid

<400> SEQUENCE: 13

His Xaa Asn Trp Xaa
1               5
```

```
<210> SEQ ID NO 14
<211> LENGTH: 5
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid

<400> SEQUENCE: 14

His Xaa Asn Trp Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 15

His Xaa Asn Trp Tyr
1               5

<210> SEQ ID NO 16
<211> LENGTH: 5
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 16

His Xaa Asn Trp Trp
1               5

<210> SEQ ID NO 17
<211> LENGTH: 5
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 17

His Xaa Asn Trp Leu
1               5

<210> SEQ ID NO 18
<211> LENGTH: 5
<212> TYPE: PRT
<213> ORGANISM: Artificial Sequence
<220> FEATURE:
<223> OTHER INFORMATION: ASPD-interacting motif/peptide
```

```
<220> FEATURE:
<221> NAME/KEY: MISC_FEATURE
<222> LOCATION: (2)..(2)
<223> OTHER INFORMATION: Xaa=Phe or Leu

<400> SEQUENCE: 18

His Xaa Asn Trp Asp
1               5

<210> SEQ ID NO 19
<211> LENGTH: 6
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Arg, His, or Lys
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid

<400> SEQUENCE: 19

Xaa Xaa Asn Trp Xaa Trp
1               5

<210> SEQ ID NO 20
<211> LENGTH: 6
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid

<400> SEQUENCE: 20

His Xaa Asn Trp Xaa Trp
1               5

<210> SEQ ID NO 21
<211> LENGTH: 6
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid

<400> SEQUENCE: 21

His Xaa Asn Trp Xaa Trp
1               5
```

```
<210> SEQ ID NO 22
<211> LENGTH: 6
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 22

His Xaa Asn Trp Tyr Trp
1               5

<210> SEQ ID NO 23
<211> LENGTH: 6
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 23

His Xaa Asn Trp Trp Trp
1               5

<210> SEQ ID NO 24
<211> LENGTH: 6
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 24

His Xaa Asn Trp Leu Trp
1               5

<210> SEQ ID NO 25
<211> LENGTH: 6
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 25

His Xaa Asn Trp Asp Trp
1               5

<210> SEQ ID NO 26
<211> LENGTH: 7
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Arg, His, or Lys
```

```
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 26

Xaa Xaa Asn Trp Xaa Xaa Trp
1               5

<210> SEQ ID NO 27
<211> LENGTH: 7
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 27

His Xaa Asn Trp Xaa Xaa Trp
1               5

<210> SEQ ID NO 28
<211> LENGTH: 7
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 28

His Xaa Asn Trp Xaa Xaa Trp
1               5

<210> SEQ ID NO 29
<211> LENGTH: 8
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Arg, His, or Lys
```

```
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 29

Xaa Xaa Asn Trp Xaa Xaa Xaa Trp
1               5

<210> SEQ ID NO 30
<211> LENGTH: 8
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=hydrophobic amino acid or Gly
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 30

His Xaa Asn Trp Xaa Xaa Xaa Trp
1               5

<210> SEQ ID NO 31
<211> LENGTH: 8
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu
<220> FEATURE:
<221> NAME/KEY: MISC_FEATURE
<222> LOCATION: (5)..(5)
<223> OTHER INFORMATION: Xaa=Trp, Tyr, Asp, or hydrophobic amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 31

His Xaa Asn Trp Xaa Xaa Xaa Trp
1               5

<210> SEQ ID NO 32
<211> LENGTH: 8
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu
```

```
<400> SEQUENCE: 32

His Xaa Asn Trp Tyr Asn Leu Trp
1               5

<210> SEQ ID NO 33
<211> LENGTH: 8
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 33

His Xaa Asn Trp Trp His Ser Trp
1               5

<210> SEQ ID NO 34
<211> LENGTH: 8
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (2)..(2)
<223> OTHER INFORMATION: Xaa=Phe or Leu

<400> SEQUENCE: 34

His Xaa Asn Trp Leu Ser Trp Phe
1               5

<210> SEQ ID NO 35
<211> LENGTH: 12
<212> TYPE: PRT
<213> ORGANISM: Artificial Sequence
<220> FEATURE:
<223> OTHER INFORMATION: ASPD-interacting motif/peptide

<400> SEQUENCE: 35

His Phe Asn Trp Tyr Asn Leu Trp Arg Val Gln Tyr
1               5                   10

<210> SEQ ID NO 36
<211> LENGTH: 12
<212> TYPE: PRT
<213> ORGANISM: Artificial Sequence
<220> FEATURE:
<223> OTHER INFORMATION: ASPD-interacting motif/peptide

<400> SEQUENCE: 36

His Leu Asn Trp Trp His Ser Trp Tyr Pro Ala Arg
1               5                   10

<210> SEQ ID NO 37
<211> LENGTH: 12
<212> TYPE: PRT
<213> ORGANISM: Artificial Sequence
<220> FEATURE:
<223> OTHER INFORMATION: ASPD-interacting motif/peptide

<400> SEQUENCE: 37

His Leu Asn Trp Leu Ser Trp Phe Pro Ser Arg His
1               5                   10
```

```
<210> SEQ ID NO 38
<211> LENGTH: 5
<212> TYPE: PRT
<213> ORGANISM: Artificial Sequence
<220> FEATURE:
<223> OTHER INFORMATION: ASPD-interacting motif/peptide

<400> SEQUENCE: 38

His Phe Asn Trp Asp
1               5

<210> SEQ ID NO 39
<211> LENGTH: 6
<212> TYPE: PRT
<213> ORGANISM: Artificial Sequence
<220> FEATURE:
<223> OTHER INFORMATION: ASPD-interacting motif/peptide

<400> SEQUENCE: 39

His Phe Asn Trp Asp Trp
1               5

<210> SEQ ID NO 40
<211> LENGTH: 12
<212> TYPE: PRT
<213> ORGANISM: Artificial Sequence
<220> FEATURE:
<223> OTHER INFORMATION: ASPD-interacting motif/peptide (control)

<400> SEQUENCE: 40

His His Leu Trp Arg Pro Phe Trp Trp Ala Glu Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: ASPD-interacting motif/peptide (control)

<400> SEQUENCE: 41

His Ser Trp Trp Ser Ser Trp Leu Arg Pro Gly Thr
1               5                   10

<210> SEQ ID NO 42
<211> LENGTH: 4
<212> TYPE: PRT
<213> ORGANISM: Artificial Sequence
<220> FEATURE:
<223> OTHER INFORMATION: ASPD-interacting motif/peptide

<400> SEQUENCE: 42

His Phe Asn Trp
1

<210> SEQ ID NO 43
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=hydrophobic amino acid or Gly
```

```
<220> FEATURE:
<221> NAME/KEY: MISC_FEATURE
<222> LOCATION: (2)..(2)
<223> OTHER INFORMATION: Xaa=Asn, Gln, Ser, Thr, Cys, His, Tyr, Trp,
      Phe, or Tyr
<220> FEATURE:
<221> NAME/KEY: MISC_FEATURE
<222> LOCATION: (3)..(3)
<223> OTHER INFORMATION: Xaa=Trp, Phe, or Tyr
<220> FEATURE:
<221> NAME/KEY: MISC_FEATURE
<222> LOCATION: (4)..(4)
<223> OTHER INFORMATION: Xaa=Trp, Tyr, Asp, or hydrophobic amino acid

<400> SEQUENCE: 43

Xaa Xaa Xaa Xaa
1

<210> SEQ ID NO 44
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=hydrophobic amino acid or Gly
<220> FEATURE:
<221> NAME/KEY: MISC_FEATURE
<222> LOCATION: (4)..(4)
<223> OTHER INFORMATION: Xaa=Trp, Tyr, Asp, or hydrophobic amino acid

<400> SEQUENCE: 44

Xaa Asn Trp Xaa
1

<210> SEQ ID NO 45
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Phe or Leu
<220> FEATURE:
<221> NAME/KEY: MISC_FEATURE
<222> LOCATION: (4)..(4)
<223> OTHER INFORMATION: Xaa=Trp, Tyr, Asp, or hydrophobic amino acid

<400> SEQUENCE: 45

Xaa Asn Trp Xaa
1

<210> SEQ ID NO 46
<211> LENGTH: 4
<212> TYPE: PRT
<213> ORGANISM: Artificial Sequence
<220> FEATURE:
<223> OTHER INFORMATION: ASPD-interacting motif/peptide
<220> FEATURE:
<221> NAME/KEY: MISC_FEATURE
<222> LOCATION: (1)..(1)
<223> OTHER INFORMATION: Xaa=Phe or Leu

<400> SEQUENCE: 46

Xaa Asn Trp Asp
1
```

```
<210> SEQ ID NO 47
<211> LENGTH: 4
<212> TYPE: PRT
<213> ORGANISM: Artificial Sequence
<220> FEATURE:
<223> OTHER INFORMATION: ASPD-interacting motif/peptide

<400> SEQUENCE: 47

Phe Asn Trp Asp
1
```